United States Patent
Heikenfeld et al.

(10) Patent No.: US 9,867,539 B2
(45) Date of Patent: Jan. 16, 2018

(54) SWEAT SENSING DEVICE COMMUNICATION SECURITY AND COMPLIANCE

(71) Applicant: Eccrine Systems, Inc., Cincinnati, OH (US)

(72) Inventors: Jason Heikenfeld, Cincinnati, OH (US); Daniel P. Rose, Cincinnati, OH (US); Ian Papautsky, Willowbrook, IL (US); Wenjing Kang, Malden, MA (US); Xiao Wang, Malden, MA (US); Michael Ratterman, South Lebanon, OH (US)

(73) Assignee: Eccrine Systems, Inc., Cincinnati, OH (US)

( * ) Notice: Subject to any disclaimer, the term of this patent is extended or adjusted under 35 U.S.C. 154(b) by 0 days.

(21) Appl. No.: 15/362,229

(22) Filed: Nov. 28, 2016

(65) Prior Publication Data
US 2017/0100035 A1   Apr. 13, 2017

Related U.S. Application Data

(63) Continuation of application No. PCT/US2015/055756, filed on Oct. 15, 2015.
(Continued)

(51) Int. Cl.
*A61B 5/05*   (2006.01)
*A61B 5/00*   (2006.01)
(Continued)

(52) U.S. Cl.
CPC ............ *A61B 5/0022* (2013.01); *A61B 5/117* (2013.01); *A61B 5/14517* (2013.01);
(Continued)

(58) Field of Classification Search
CPC ............ A61B 10/0064; A61B 5/14521; A61B 5/14517; A61B 5/746; A61B 5/00;
(Continued)

(56) References Cited

U.S. PATENT DOCUMENTS

| 4,190,060 A | 2/1980 | Greenleaf et al. |
| 5,437,999 A | 8/1995 | Diebold et al. |
| (Continued) | | |

FOREIGN PATENT DOCUMENTS

| EP | 0634215 A1 | 1/1995 |
| EP | 1500937 A1 | 1/2005 |
| (Continued) | | |

OTHER PUBLICATIONS

Baker, et al. "Comparison of regional patch collection vs. whole body washdown for measuring sweat sodium and potassium loss during exercise", *The American Physiological Society*, pp. 887-895, 2009.
(Continued)

*Primary Examiner* — Navin Natnithithadha
*Assistant Examiner* — Eric Messersmith
(74) *Attorney, Agent, or Firm* — Kilpatrick Townsend & Stockton LLP

(57) ABSTRACT

The invention addresses confounding difficulties involving continuous sweat analyte measurement. Specifically, the present invention provides: at least one component capable of monitoring whether a sweat sensing device is in sufficient contact with a wearer's skin to allow proper device operation; at least one component capable of monitoring whether the device is operating on a wearer's skin; at least one means of determining whether the device wearer is a target individual within a probability range; at least one component capable of generating and communicating alert messages to the device user(s) related to: wearer safety, wearer physi-
(Continued)

ological condition, compliance with a requirement to wear a device, device operation; compliance with a behavior requirement, or other purposes that may be derived from sweat sensor data; and the ability to utilize aggregated sweat sensor data that may be correlated with information external to the device to enhance the predictive capabilities of the device.

20 Claims, 12 Drawing Sheets

Related U.S. Application Data

(60) Provisional application No. 62/064,009, filed on Oct. 15, 2014.

(51) Int. Cl.
*A61B 5/145* (2006.01)
*A61B 5/117* (2016.01)
*H04Q 9/00* (2006.01)
*G06F 19/00* (2011.01)

(52) U.S. Cl.
CPC ...... *A61B 5/14521* (2013.01); *A61B 5/14546* (2013.01); *A61B 5/4266* (2013.01); *A61B 5/4845* (2013.01); *A61B 5/6843* (2013.01); *A61B 5/7275* (2013.01); *A61B 5/746* (2013.01); *H04Q 9/00* (2013.01); *A61B 2562/0214* (2013.01); *A61B 2562/08* (2013.01); *G06F 19/345* (2013.01); *H04Q 2209/40* (2013.01)

(58) Field of Classification Search
CPC ....... A61B 5/117; A61B 5/145; A61B 5/0022; A61B 5/4266; A61B 5/14546; A61B 5/4845; A61B 5/7275; A61B 2562/0214; A61B 2562/08; H04Q 9/00; H04Q 2209/40; G06F 19/345
See application file for complete search history.

(56) References Cited

U.S. PATENT DOCUMENTS

| | | | |
|---|---|---|---|
| 5,531,870 A | 7/1996 | Cha | |
| 5,690,893 A | 11/1997 | Ozawa et al. | |
| 6,175,752 B1 * | 1/2001 | Say | A61M 5/1723 128/903 |
| 6,269,265 B1 | 7/2001 | Anderson | |
| 7,044,911 B2 | 5/2006 | Drinan et al. | |
| 7,383,072 B2 | 6/2008 | Edmonson et al. | |
| 7,800,494 B2 | 9/2010 | Kim | |
| 2004/0215098 A1 | 10/2004 | Barton et al. | |
| 2004/0260154 A1 | 12/2004 | Sidelnik et al. | |
| 2005/0106713 A1 | 5/2005 | Phan et al. | |
| 2005/0228297 A1 | 10/2005 | Banet et al. | |
| 2005/0280531 A1 | 12/2005 | Fadem et al. | |
| 2006/0009697 A1 | 1/2006 | Banet et al. | |
| 2007/0027383 A1 | 2/2007 | Peyser et al. | |
| 2008/0306362 A1 | 12/2008 | Davis | |
| 2009/0159442 A1 | 6/2009 | Collier et al. | |
| 2009/0270704 A1 | 10/2009 | Peyser et al. | |
| 2010/0063372 A1 | 3/2010 | Potts et al. | |
| 2010/0130843 A1 | 5/2010 | Caceres Galvez et al. | |
| 2011/0004072 A1 | 1/2011 | Fletcher et al. | |
| 2011/0054273 A1 | 3/2011 | Omoda | |
| 2011/0275918 A1 | 11/2011 | Yamashita et al. | |
| 2012/0119906 A1 | 5/2012 | Kountotsis | |
| 2012/0191147 A1 | 7/2012 | Rao et al. | |
| 2013/0245388 A1 | 9/2013 | Rafferty et al. | |
| 2013/0317318 A1 | 11/2013 | Tartz et al. | |
| 2014/0012114 A1 | 1/2014 | Zevenbergen et al. | |
| 2014/0221792 A1 | 8/2014 | Miller et al. | |
| 2015/0057515 A1 | 2/2015 | Hagen et al. | |
| 2015/0112164 A1 | 4/2015 | Heikenfeld et al. | |
| 2015/0112165 A1 | 4/2015 | Heikenfeld | |
| 2015/0289820 A1 | 10/2015 | Miller et al. | |
| 2017/0100071 A1 | 4/2017 | Heikenfeld | |
| 2017/0100072 A1 | 4/2017 | Heikenfeld | |
| 2017/0215773 A1 | 8/2017 | Heikenfeld et al. | |

FOREIGN PATENT DOCUMENTS

| | | |
|---|---|---|
| EP | 1575010 A1 | 9/2005 |
| EP | 2783725 A1 | 3/2012 |
| EP | 3206569 A2 | 8/2017 |
| WO | 90/11519 | 10/1990 |
| WO | 01/88525 A1 | 11/2001 |
| WO | 2008/058014 A2 | 5/2008 |
| WO | 2008/083687 A1 | 7/2008 |
| WO | 2010/017578 A1 | 2/2010 |
| WO | 2011008581 | 1/2011 |
| WO | 2013/111409 A1 | 8/2013 |
| WO | 2013/152087 A2 | 10/2013 |
| WO | 2015/058055 A1 | 4/2015 |
| WO | 2015/058064 A1 | 4/2015 |
| WO | 2015184065 | 12/2015 |
| WO | 2015184072 | 12/2015 |
| WO | 2015184084 | 12/2015 |
| WO | 2015184097 | 12/2015 |
| WO | 2016007944 | 1/2016 |
| WO | 2016049019 | 3/2016 |
| WO | 2016/061362 A2 | 4/2016 |

OTHER PUBLICATIONS

Fu, et al., "Controlled reagent transport in disposable 2D paper networks," Lab on a chip, Royal Society of Chemistry, vol. 10, pp. 918-920, 2010.
Heikenfeld, J., "Let Them See You Sweat", *IEEE Spectrum*, pp. 46-50 and 62-63, Nov. 2014.
Rose, et al., "Adhesive RFID Sensor Patch for Monitoring of Sweat Electrolytes", *IEEE Transactions on Biomedical Engineering.*, pp. 1-9, 2013.
Sato, et al., "Sweat secretion by human axillary apoeccrine sweat gland in vitro", *Marshall Dermatology Research Laboratories, University of Iowa College of Medicine*, pp. R181-R187, 1987.
Sonner, et al., "The microfluidics of the eccrine sweat gland, including biomarker partitioning, transport, and biosensing implications," *Biomicrofluidics*, vol. 9, No. 3, all pages, 2015.
Taylor, et al., "Regional variations in transepidermal water loss, eccrine sweat gland density, sweat secretion rates and electrolyte composition in resting and exercising humans", *Exreme Physiology & Medicine*, vol. 2, No. 4, pp. 1-29, 2013.
International Patent Application No. PCT/US2015/055756, International Search Report and Written Opinion, dated May 6, 2016, 15 pages.
International Patent Application No. PCT/US2013/035092, International Search Report, dated Dec. 3, 2013, 7 pages.
International Patent Application No. PCT/US2013/035092, Written Opinion, dated Oct. 4, 2014, 10 pages.
U.S. Appl. No. 15/362,303, filed Nov. 28, 2016, 26 pages.
U.S. Appl. No. 15/362,303, Non-Final Office Action dated Jan. 17, 2017, 17 pages.
U.S. Appl. No. 15/362,299, filed Nov. 28, 2016, 26 pages.
U.S. Appl. No. 15/362,299, Final Office Action, dated Sep. 8, 2017, 9 pages.
U.S. Appl. No. 15/362,299 , Non-Final Office Action, dated Mar. 10. 2017, 8 pages.
U.S. Appl. No. 15/362,303, Final Office Action, dated May 16, 2017. 22 pages.
U.S. Appl. No. 15/362,229, Notice of Allowance, dated Sep. 27, 2017, 11 pages.
European Patent Application No. EP15790344.4, Office Action, dated Oct. 6, 2017, 8 pages.

(56) References Cited

OTHER PUBLICATIONS

European Patent Application No. EP17172694.6, Extended European Search Report, dated Oct. 11, 2017, 8 pages.

* cited by examiner

SWEAT SENSING DEVICE COMMUNICATION SECURITY AND COMPLIANCE

CROSS-REFERENCE TO RELATED APPLICATIONS

The present application is a continuation of PCT Application No. PCT/US15/55756, filed on Oct. 15, 2015, which claims the benefit of U.S. Provisional Application No. 62/064,009, filed on Oct. 15, 2014 and which is related to PCT Application No. PCT/US13/35092, filed on Apr. 3, 2013. Each of these applications is hereby incorporated by reference in its entirety for all purposes.

BACKGROUND OF THE INVENTION

Sweat sensing technologies have enormous potential for applications ranging from athletics to neonatology, to pharmacological monitoring, to personal digital health, to name a few applications. Sweat contains many of the same biomarkers, chemicals, or solutes that are carried in blood and can provide significant information enabling one to diagnose illness, health status, exposure to toxins, performance, and other physiological attributes even in advance of any physical sign. Furthermore, sweat itself, the action of sweating, and other parameters, attributes, solutes, or features on, near, or beneath the skin can be measured to further reveal physiological information.

If sweat has such significant potential as a sensing paradigm, then why has it not emerged beyond decades-old usage in infant chloride assays for Cystic Fibrosis or in illicit drug monitoring patches? In decades of sweat sensing literature, the majority of practitioners in the art use the crude, slow, and inconvenient process of sweat stimulation, collection of a sample, transport of the sample to a lab, and then analysis of the sample by a bench-top machine and a trained expert. This process is so labor intensive, complicated, and costly that in most cases, one would just as well implement a blood draw since it is the gold standard for most forms of high performance biomarker sensing. Hence, sweat sensing has not emerged into its fullest opportunity and capability for biosensing, especially for continuous or repeated biosensing or monitoring. Furthermore, attempts at using sweat to sense "holy grails" such as glucose have not yet succeeded to produce viable commercial products, reducing the publicly perceived capability and opportunity space for sweat sensing.

Of all the other physiological fluids used for biological monitoring (e.g., blood, urine, saliva, tears), sweat has arguably the least predictable sampling rate in the absence of technology. However, with proper application of technology, sweat can be made to outperform other non-invasive or less invasive biofluids in predictable sampling.

For example, it is difficult to control saliva or tear rate without negative consequences for the user (e.g., dry eyes, tears, dry mouth, or excessive saliva while talking). Urine is also a difficult fluid for physiological monitoring, because it is inconvenient to take multiple urine samples, it is not always possible to take a urine sample when needed, and control of biomarker dilution in urine imposes further significant inconveniences on the user or test subject.

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing technology into intimate proximity with sweat as it is generated. With such an invention, sweat sensing could become a compelling new paradigm as a biosensing platform.

In particular, sweat sensors hold tremendous promise for use in workplace safety, athletic, military, and health care settings. For workplace safety and military applications, a sweat sensing device worn on the job and connected to a computer network via a reader device, such as a smart phone or other portable or stationary device, could relay crucial data about physiological conditions, or the presence of prohibited substances in the bloodstream. In health care settings, sweat sensors may continuously monitor the health of individuals, for example, patients who are restricted to bed rest or participating in a clinical trial, and communicate to a reader device or computer network, which would then compare collected data to threshold readings and alert caregivers if the individual is in need of intervention.

For these applications to be effective, however, it is crucial that a targeted individual is wearing the proper sweat sensor device, and that the device is operational. Sweat sensor devices may be deployed in various internal configurations, with devices configured for detecting a specific analyte or a group of analytes, depending on the application. If a device is placed on a different individual than the target individual, the collected information will be inapplicable to the target individual. Or, if a target individual is wearing the incorrect device for a particular application, the desired information may not be collected. Likewise, a device that has inadequate contact with the skin, or that is otherwise inoperable due to electronic or other malfunction, will not effectively collect sweat and detect the targeted analytes.

SUMMARY OF THE INVENTION

The present invention is premised on the realization that sweat can be effectively stimulated and analyzed in a single, continuous, or repeated manner inside the same device. The present invention addresses the confounding difficulties involving such analysis by assuring that a sweat sensing device is adequately secured to a wearer's skin, is operational, and that the wearer is a target individual. Specifically, the present invention provides: at least one component capable of monitoring whether a sweat sensing device is in adequate contact with a wearer's skin to allow proper operation of the sweat sensing device; at least one component capable of monitoring whether a sweat sensing device is operating on the wearer's skin; at least one means of determining whether a device is being worn by a target individual within a probability range; at least one component capable of generating and communicating alert messages to the sweat device user(s) related to: wearer safety, wearer physiological condition, compliance with a requirement to wear a device, device operation; compliance with a behavior requirement, or other purposes that may be derived from the use of sweat sensor data; and the ability to utilize aggregated sweat sensor data that may be correlated with information external to the sweat sensing device to enhance the predictive and alert capabilities of the sweat sensing device.

BRIEF DESCRIPTION OF THE DRAWINGS

The objects and advantages of the present invention will be further appreciated in light of the following detailed descriptions and drawings in which.

DEFINITIONS

Figure 1:
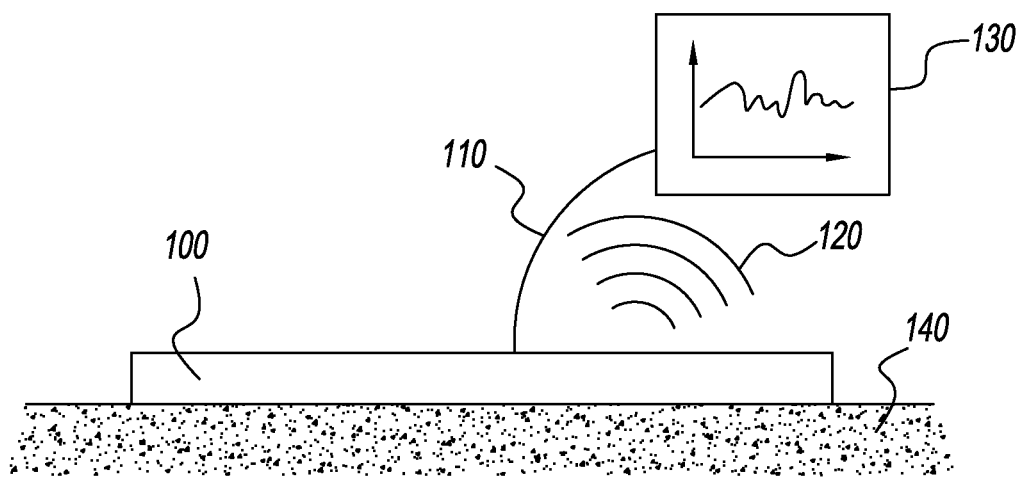
FIG. 1 is a generic representation of the present invention including a mechanism for stimulating and analyzing sweat sensor data on a singular, continuous or repeated basis.

Sweat sensor data means all of the information collected by sweat sensing device sensor(s) and communicated via the device to a user or a data aggregation location.

Correlated aggregated data means sweat sensor data that has been collected in a data aggregation location and correlated with outside information such as time, temperature, weather, location, user profile, other sweat sensor data, other wearables data, or any other relevant data.

Analyte data signature means a known set of analyte levels, ratios, or concentration trends that is correlated with a specific individual within a probability range.

Identification metrics means the various identification-related readings that may be used by a sweat sensing device to indicate within a certain probability that a target individual is wearing the device. These metrics include, without limitation, sweat analyte data metrics, proxy identification metrics, communication/location metrics, or other metrics.

Identification profile means a profile composed of two or more identification metrics and associated with an individual for use in calculating an identification probability estimate.

Identification probability estimate means the calculated probability that a person wearing a sweat sensing device is a target individual based on a comparison of identification metrics with known data about the target individual.

Compliance metric means a skin contact measurement, device operation measurement, or an identification metric.

Operation and compliance reading means the sweat sensor data collected on at least one compliance metric.

Operation and compliance alert means a message generated by the sweat sensing device and relayed to a user when an operation and compliance reading indicates a device skin contact status, an operational status, or a wearer identification status.

Safety and health reading means a measurement of at least one sweat analyte that indicates the concentration, or concentration trend, of the analyte in a wearer's sweat.

Safety and health alert means an alert generated by the sweat sensing device and relayed to a user and/or a wearer, when a safety and health reading indicates that some intervention is recommended.

Safety profile means a known set of sweat analyte levels, ratios, or concentration trends that indicates with a certain probability that a wearer needs intervention, such as from a health condition.

Behavioral profile means a known set of sweat analyte levels, ratios, or concentration trends that indicates with a certain probability that a wearer is in compliance with a behavioral program, such as a drug regimen.

DETAILED DESCRIPTION OF THE INVENTION

The detailed description of the present invention will be primarily be, but not entirely be, limited to subcomponents, subsystems, sub methods, of wearable sensing devices, including devices dedicated to sweat sensing. Therefore, although not described in detail here, other essential features which are readily interpreted from or incorporated along with the present invention shall be included as part of the present invention. The specification for the present invention provides examples to portray inventive steps, but which will not necessarily cover all possible embodiments commonly known to those skilled in the art. For example, the described invention will not necessarily include all obvious features needed for operation, examples being a battery or power source which is required to power electronics, or for example, a wax paper backing that is removed prior to applying an adhesive patch, or for example, a particular antenna design that allows wireless communication with a particular external computing and information display device.

With reference to FIG. 1, a sweat sensing device 100 is placed on or near skin 140 (shown), or in an alternate embodiment is simply fluidically connected to skin or regions near skin through microfluidics or other suitable techniques (not shown). A complete enablement of such a device is described by Rose and Heikenfeld in the article in press for publication in the journal IEEE Transactions on Biomedical Engineering, titled "Adhesive RFID Sensor Patch for Monitoring of Sweat Electrolytes". The present invention applies at least to any type of sweat sensing device that stimulates and/or measures sweat, its solutes, solutes that transfer into sweat from skin, a property of or things on the surface of skin, or properties or things beneath the skin, or measures something about the surrounding; environment including humidity, temperature, motion, or other external factors to be measured. The present invention applies to sweat sensing devices which can take on forms that include patches, bands, straps, portions of clothing, wearables, or any suitable mechanism that reliably brings sweat stimulating, sweat collecting, and/or sweat sensing technology into intimate proximity with sweat as it is generated. Some embodiments of the present invention utilize adhesives to hold the device near the skin, but devices could also be held by other mechanisms that hold the device secure against the skin, such as a strap or embedding the device in a helmet or other headgear. Certain embodiments of the present invention show sensors as simple individual elements, it is understood that many sensors such as potentiometric, amperometric, impedimetric, and others, require two or more electrodes, reference electrodes, or additional supporting technology or features which are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is measuring, for example: a sweat sensor; an impedance sensor; a sweat volume sensor; a sweat generation rate sensor; or a solute generation rate sensor. The present invention includes all direct or indirect mechanisms of sweat stimulation, including but not limited to sweat stimulation by heat, pressure, electricity, iontophoresis or diffusion of chemical sweat stimulants, orally or injected drugs that stimulate sweat, stimuli external to the body, cognitive activity, or physical activity, or other sweat responses to external stimuli. Certain embodiments of the present invention show sub-components of sweat sensing devices that would require additional obvious sub-components for various applications (such as a battery, or a counter electrode for iontophoresis). These additional sub-components are not critical to the inventive step of the present invention, and for purpose of brevity and focus on inventive aspects, are not explicitly shown in the diagrams or described do the embodiments of the present invention.

With further reference to FIG. 1, the arrangement and description of the device is an example embodiment only, and other obvious configurations and applications are included within spirit of the present invention. The device 100 is in wired communication 110 or wireless communication 120 with an AC or battery-powered reader device 130, and placed on skin 140. In one embodiment of the present invention, the reader device 130 would be a smart phone, or other portable electronic device. In another embodiment, the reader device is a companion transceiver placed at bedside, mounted in a commercial or military vehicle, or widely distributed in locations that are supplied with electrical power. In another embodiment, the reader device is a portable electronic device or companion transceiver capable of secure two-way communication with the sensor and secure two-way communication with a computer network, such as a local area network or the Internet via a wireless router and/or a cellular data network. In alternate embodiments the device 100 and device 130 can be combined (not shown).

The device may include RFID, or may include wireless protocol such as Bluetooth, or the device may use alternate communication or power strategies to communicate with a reader device in proximity to the device. The sensor can include a thin layer battery and provide its own power source, and thus not rely on RFID. Both RFID and Bluetooth can be used in conjunction, where RFID can charge the battery when provided the proper near field communications. The device may also include means of signal amplification to improve signal quality communicated to the reader device, and to improve transmission distance to the reader device. Other biomarker sensing methods and sweat transport methods may be included, so long as they provide the same capability of continuous or semi-continuous monitoring of sweat biomarkers.

The sweat sensing device disclosed herein also includes computing and data storage capability sufficient to operate the device, which incorporates the ability to conduct communication among device components, to perform data aggregation, and to execute algorithms capable of analyzing data and generating alert messages. This computing capability may be fully or partially located on the device, on the reader device, or on a connected computer network.

The sweat sensing device may also include data aggregation and monitoring capability. Such data aggregation may include collecting all of the sweat sensor data generated by sweat sensing devices. The aggregated data may be de-identified from individual wearers, or may remain associated with an individual wearer. Such data may also be correlated with outside information, such as the time, date, weather conditions, activity performed by the individual, the individual's mental and physical performance during the data collection, the proximity to significant health events experienced by the individual, the individual's age or sex, the individual's health history, data from other wearable devices, such as those measuring galvanic skin response, pulse oximetry, heart rate, etc., or other relevant information. The data collected may be made accessible via secure website portal to allow sweat device users to perform safety, compliance and/or care monitoring of target individuals. In an alternative embodiment, the data may be made accessible via application programming interface ("API"), which would allow sweat sensor data to be integrated with a user's existing safety, compliance and care monitoring systems, such as an employer's on-shift monitoring system. The sweat sensor data monitored by the user may include real-time data, trend data, or may also include aggregated sweat sensor data drawn from the device database and correlated to a particular user, a user profile (such as age, sex or fitness level), weather condition, activity, combined analyte profile, or other relevant metric. Trend data, such as a target individual's hydration level over time, may be used to predict future performance, or the likelihood of an impending physiological event. Such predictive capability can be enhanced by using correlated aggregated data, which would allow the user to compare an individual's historical analyte and external data profiles to a real-time situation as it progresses, or even to compare thousands of similar analyte and external data profiles from other individuals to the real-time situation. Sweat sensor data may also be used to identify wearers that are in need of additional monitoring or instruction, such as to maintain the proper hydration levels, or to adhere to a drug regimen. Sweat sensor data may be used to supply information for incentive systems by tracking an individual wearer's performance on various metrics. For example, an athletic coach may track a player's efforts to maintain proper hydration or electrolyte levels, or an employer may track positive safety results over one or more incentive cycles. Incentive system information could then be relayed to supervisory management and tied to financial incentives for the target individual. The disclosed uses of aggregated data are for illustration purposes only, and do not limit other potential sources or applications available for such data, which are within the spirit of the present invention.

Figure 2:
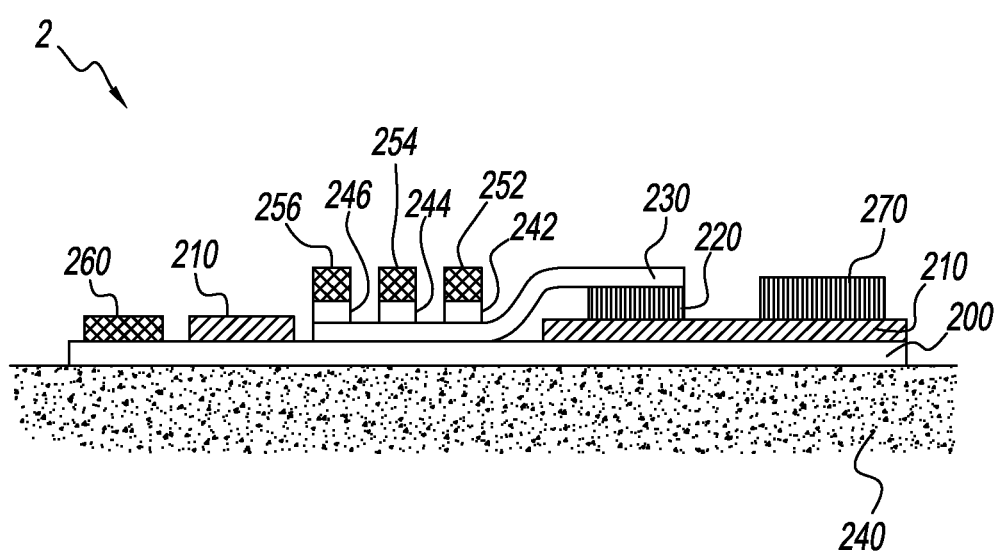
FIG. 2 is an example embodiment of at least a portion of a device of the present invention including a mechanism for generating sweat sensor data that may be used to develop and communicate alert messages.

FIG. 2 is an example embodiment of at least a portion of a device of the present invention capable of ensuring device security and compliance through the use of various means. As shown in FIG. 2, a sweat sensing device 2 positioned on skin 240 by an adhesive layer 200 bonded to fluid impermeable substrate 210. Substrate 210 holds electronics 270, one or more sensors 220 (one shown), a microfluidic component 230, coupled to one or more sweat pads 242, 244, 246. Each pad has a source of chemical sweat stimulant, such as pilocarpine, and independently controlled iontophoresis electrode(s) 252, 254, 256. There is also one or more counter electrode(s) 260. The sweat sensor 220 can be a gate-exposed SiCMOS chip having three or more identical chem-FETs per biomarker. Sub-micron SiCMOS allow for MHz impedance spectroscopy. Sensors are separated spatially into subgroups of identical sensors, or large sensor arrays can be formed using techniques such as photo-initiated chemical patterning. Arrays of biomarker-specific sensors allow for continuous monitoring of multiple physiological conditions. Thus, in operation, the electronics 270 would activate one or more electrodes 252, 254, 256. This will cause the skin to generate sweat, which will be transferred through the microfluidic structures 230, directed to the sensor 220.

In addition to sweat generation, the electrodes 252, 254, 256, with counter electrode 260 may also be used to measure skin and/or body impedance in order to determine whether the device is in adequate contact with the skin. In other embodiments, the device 2 may be configured with two or more skin facing electrodes dedicated to determining skin and/or body impedance (not shown), as are known to those skilled in the art of electrophysiology. Similarly, in other embodiments, at least one capacitive sensor electrode (not shown), also as known in the art of electrophysiology, may be placed on selected locations on the skin-facing side of the device, and would convey information about the distance between the sensor and the skin. The skin proximity readings generated by the capacitive sensor(s) would therefore indicate whether the device is in adequate contact with a wearer's skin.

Figure 3:
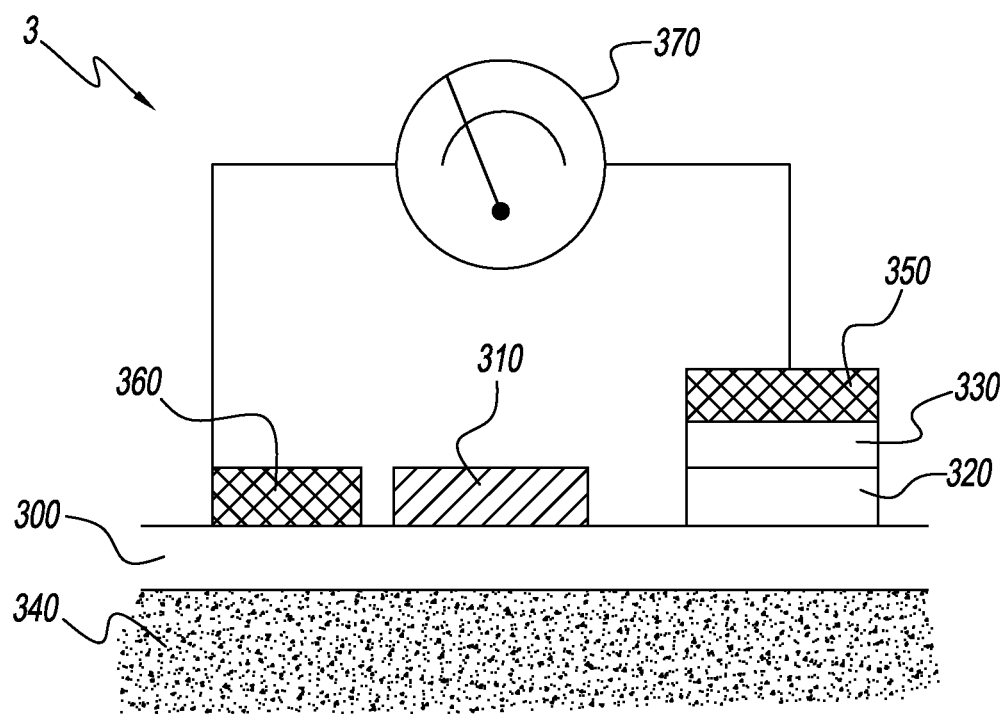
FIG. 3 is an example embodiment of at least a portion of a device of the present invention including a mechanism for determining adequate skin contact between the device and a wearer.

FIG. 3 is applicable to any of the devices of FIGS. 1-2. If electrode/pad contact to the skin is or becomes inadequate, this can be detected as an increase in impedance and the sweat sensing device can send an alert message to the user. The sweat sensing device 3 affixed to skin 340 by adhesive 300 senses impedance of the contact of the electrode 350 (with chemical stimulant source 330 and microfluidic component 320) with the skin 340 or the contact of counter electrode 360 with the skin 340 where "contact" refers to direct contact or indirect contact but which has adequate and/or uniform electrical conduction with the skin. Measurement of electrical impedance includes obvious related measures such as voltage or current, which also give a measure of impedance. If the impedance exceeds a preset limit by circuit 370, the device sends an alert to the user.

With reference to FIGS. 4A to 4D, the sweat sensing device described above may generate operation and compliance alerts to inform the device user whether a sweat sensing device (1) is in adequate contact with a wearer's skin, (2) is operating on the wearer's skin, or (3) the wearer is a target individual. Alerts may be communicated to the user via email, SMS messaging, pager, automated phone call, or callbacks to other systems. The device may conduct continuous or periodic operation and compliance readings to determine if the device is in contact with the skin, or to determine if the device is functioning on the skin of the target individual. If the sweat sensing device determines that the device is not adequately contacting the skin, the device could relay a signal to user directly or via computer network. Likewise, if the sweat sensor data, or other data, did not match a profile indicating operation on the skin, the device could relay that information. The sweat sensing device user would accordingly receive an alert message that a device is no longer operative. The device may also conduct identification readings using any of the herein disclosed means to determine the identification probability estimate for the target individual. If the sweat sensing device determined that the identification probability estimate were below a certain threshold, it could generate an operation and compliance alert that the target individual is not wearing the device.

Various means may be used to determine the appropriate time to initiate operation and compliance readings. These may be conducted continuously whenever a device is detected to be in use by the device, or if the device determines that a target individual should be wearing a device at a particular time. For example, the reader device may employ an API to communicate with an employer's on-shift system to determine if a target employee is on the job, and therefore ought to be wearing a device. In another example, a trucking company's sweat sensing device could determine through changing location data sensed by a companion transceiver that a target employee was operating a tractor-trailer, triggering the initiation of operation and compliance readings. The sweat sensing device could also integrate other data to determine whether to issue an operation and compliance alert, such as the current weather, the time of day, or the day of the week.

Figure 4A:
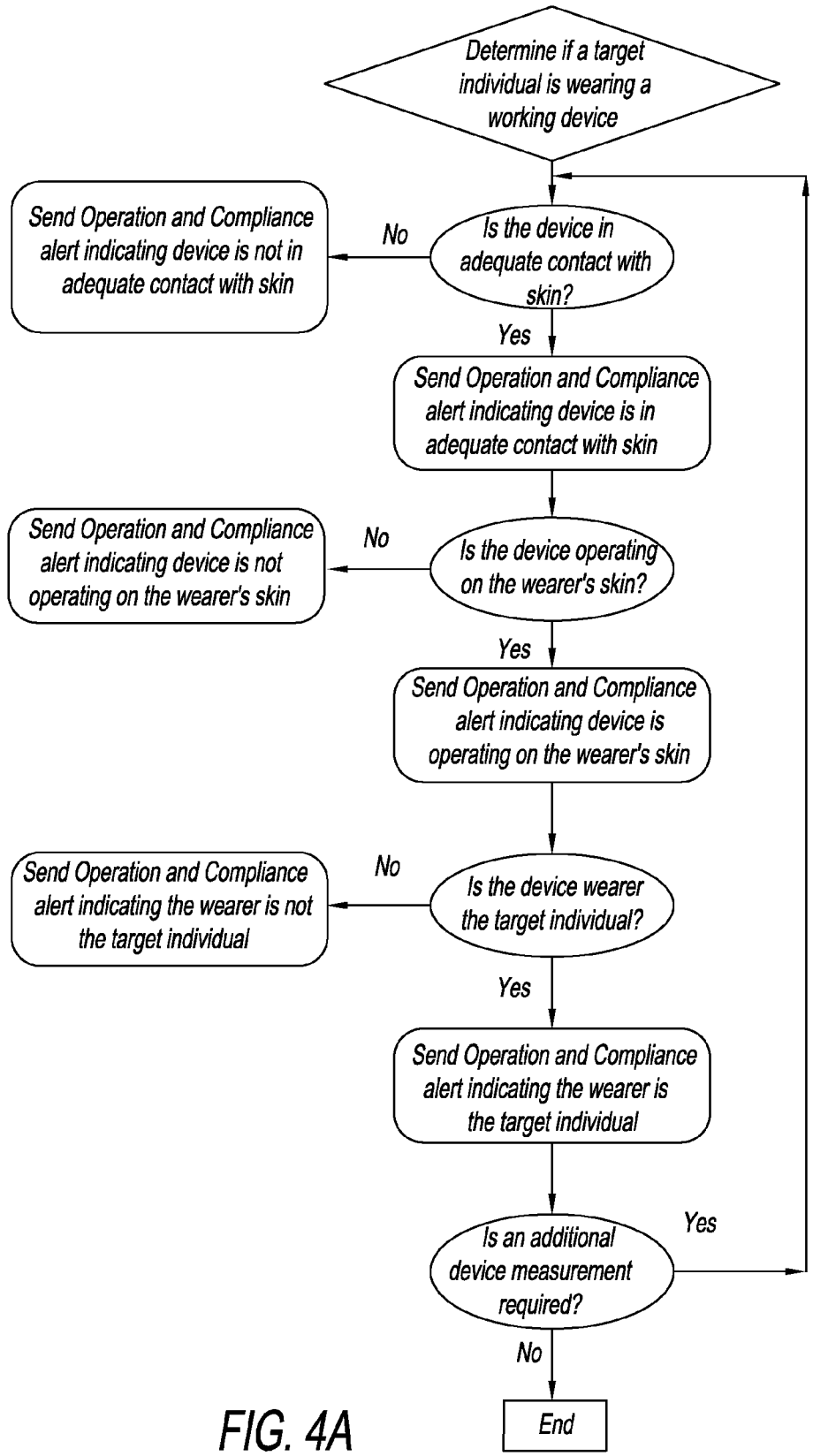
FIG. 4A is an example chart representing a method by which the present invention may determine whether a target individual is wearing a working device, and issue an appropriate operation and compliance alert.
Figure 4B:
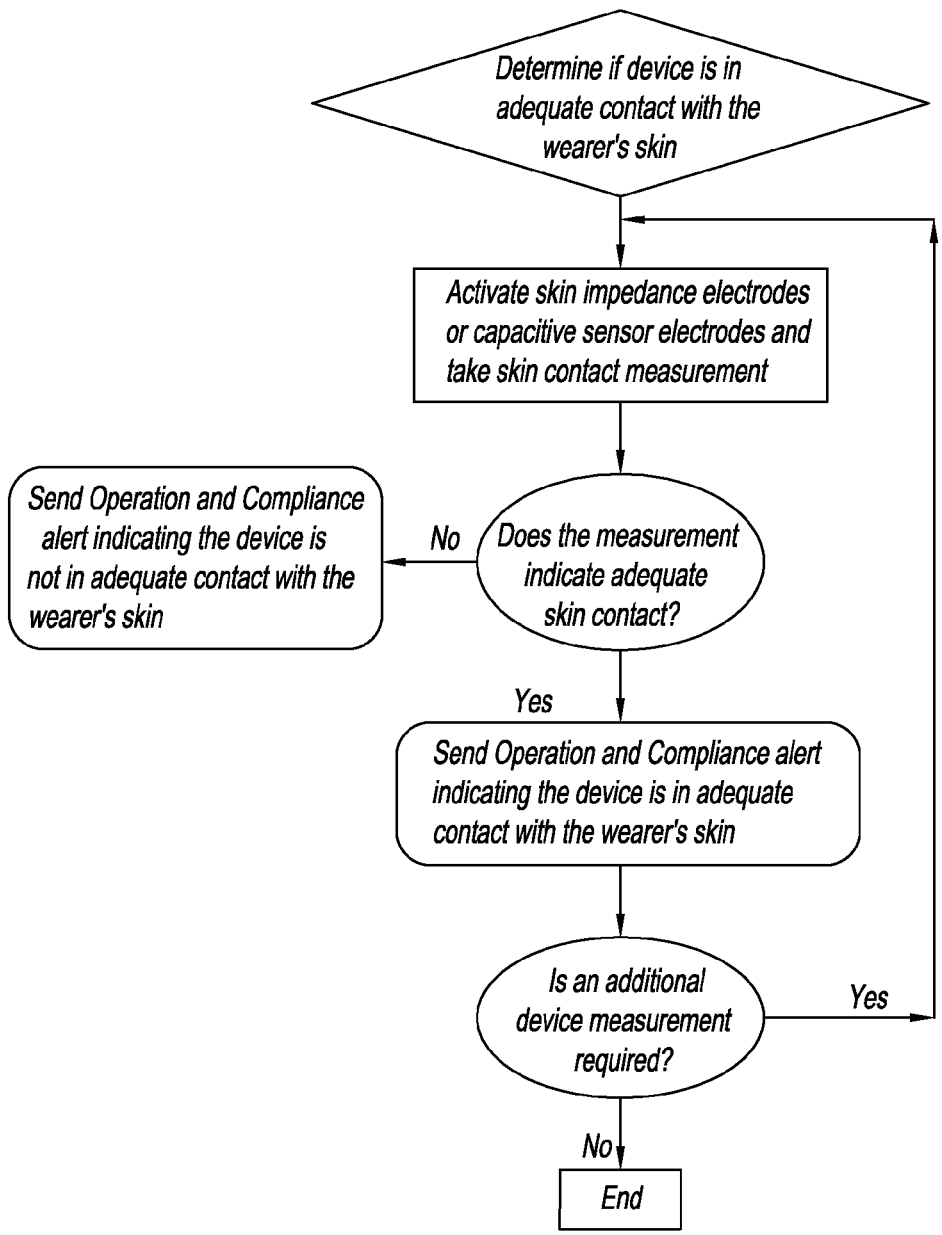
FIG. 4B is an example chart representing a subset of the method depicted in FIG. 4A by which the present invention may determine if a device is in adequate contact with a wearer's skin.

With reference to FIG. 4B, the sweat sensing device uses onboard impedance or capacitive sensors to determine if the device is in adequate contact with the wearer's skin to allow proper device function. Inadequate contact can indicate that the device has been removed by the user, or has become detached from the skin for other reasons. Additionally, inadequate skin contact can cause undesirable effects upon the skin or with the function of the device. If the device is not in adequate contact with the wearer's skin, the device will send a negative operation and compliance alert. If the device measurements indicate that the device is adequately secured to skin, an operation and compliance alert conveying that information may be sent, and the sweat sensing device will proceed to verify the other operation and compliance elements. The device may be programmed to record and track the time(s) at which a sweat sensor is in contact with the skin, as well as the time(s) at which the sweat sensor is no longer in skin contact. The device can also be programmed to sense skin contact continuously, or periodically, for example, on a daily or hourly basis.

Figure 4C:
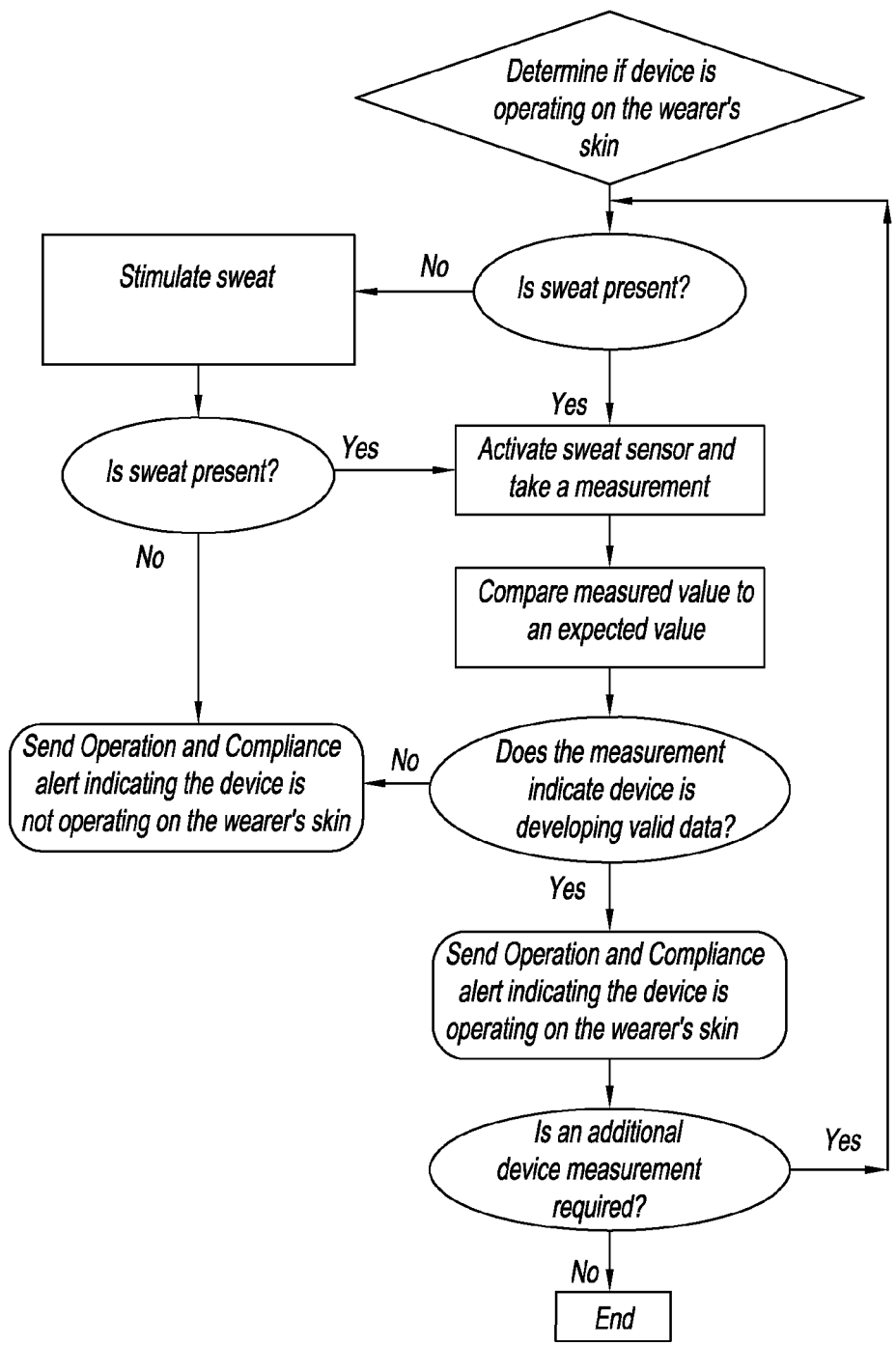
FIG. 4C is an example chart representing a subset of the method depicted in FIG. 4A by which the present invention may determine whether a device is operating on a wearer's skin.

With reference to FIG. 4C, once the device confirms it has adequate contact with a wearer's skin, it may assess whether the device is operating on the wearer's skin. When the device begins operation, it will be able to determine if the device is actually generating sweat data. For example, the device could determine whether sweat is present by taking a measurement of galvanic skin response or by measuring sweat generation rate. Additionally, sweat analyte measurements can be used to distinguish genuine sweat data from counterfeit data. Sweat analytes change in predictable ways to increases or decreases in sweat rate. For example, when sweat rate increases, $Na^+$ and concentrations in sweat typically increase, while $K^+$ concentrations stay relatively constant with sweat rate. These trending measurements would be difficult to reproduce artificially, for example, if a wearer were trying to avoid compliance by introducing other fluids to the sweat sensing device. In some embodiments, the device may also determine if the device has been placed on a body location that is appropriate for the particular device application sought by the device user. Eccrine sweat pore distribution varies throughout the body, as does the readiness with which body locations begin sweating in response to stimulus, as is discussed in further detail in Z. Sonner, et al., "The microfluidics of the eccrine sweat gland, including biomarker partitioning, transport, and biosensing implications," *Biomicrofluidics* 9, 031301 (2015); doi: 10.1063/1.4921039. Therefore, sweat rates and volumes as detected by a sweat sensing device may used to determine if a device has been applied to the correct area of the body.

Figure 4D:
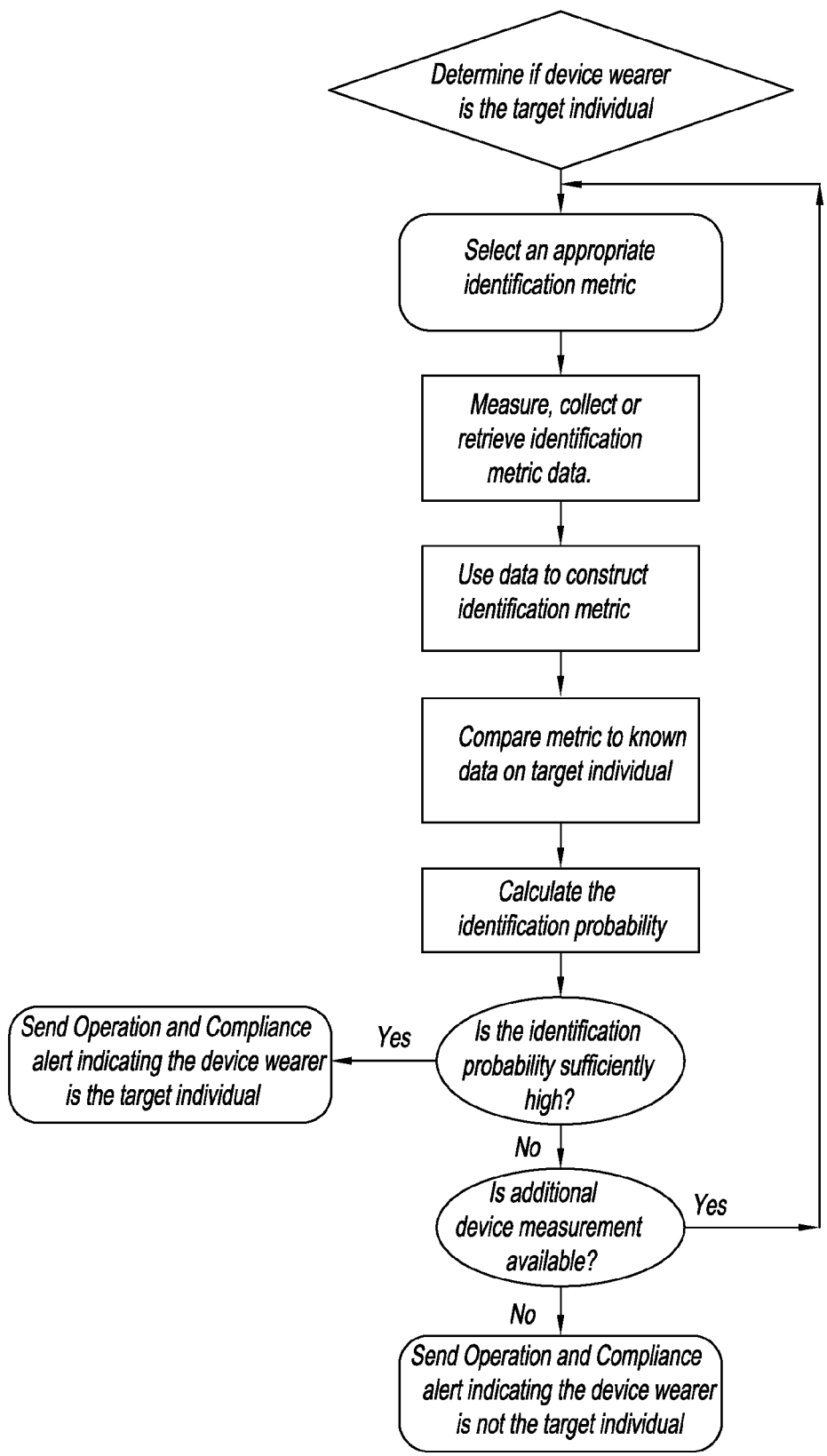
FIG. 4D is an example chart representing a subset of the method depicted in FIG. 4A by which the present invention may determine if the device wearer is a target individual.

With reference to FIG. 4D, in an example embodiment, the device may also determine whether a device wearer is likely a target individual from whom the device user desires to collect sweat data. The sweat sensing device would take readings on a selected identification metric, and would then compare that measurement to an identification signature used for the target individual. Based on this comparison, the device would calculate an identification probability estimate characterizing the probability that the wearer is the target individual. If the desired certainty about the wearer's identity has not been reached, and the device has another identification metric available, the device will measure another identification metric and calculate a new identification probability estimate. The process would continue until either the device has exhausted all of its available identification metrics, or the wearer has been positively or negatively identified as the target individual with sufficient certainty for the application. The device would then send an operation and compliance alert indicating whether or not the wearer is the target individual.

A unique identification signature for a target individual may be developed by using a sweat sensing device to generate readings for at least one of the identification metrics discussed herein. A device user would collect sufficient data on the identification metric to build a robust signature characteristic of the individual, such as a characteristic sweat RNA content. For the development of the identification signature, it will be particularly important to ensure that the target individual is actually wearing the sweat sensing device and that the collected data is accurate. For example, the device(s) used to develop the identification signature may be applied under supervision, and the target individual may need to wear the device under controlled physical conditions optimized for accurate reading, such as a climate-controlled room, or while performing set physical or mental tasks. The sweat sensing device may calculate an identification signature at the time of first use of a sweat sensor, or over multiple sweat sensor uses. The user may also develop the identification signature by some combination of the above methods. In alternative embodiments, the sweat sensing device may not develop a unique identification signature for a target individual, but instead would use an identification signature composed of relevant known general characteristics of the target individual, such as age, fitness level, or sex.

When the sweat sensing device has more than one identification metric available, the device will combine the identification probability estimates for each metric to calculate a new combined identification probability estimate. The device will use an algorithm to perform a weighted aggregation of the separate identification probability estimates, thereby increasing the overall probability of identification. The use of multiple identification metrics, therefore, will greatly increase the device's ability to determine if a wearer is a target individual, even where each identification metric alone is of limited value for distinguishing among individuals. The higher identification probability estimate will correlate with increased certainty that a target individual is, or is not, wearing the device and correspondingly reduce the incidence of false warnings generated by the device.

Designing an algorithm capable of performing an aggregation of separate identification probability estimates is known by persons skilled in the art of statistical analysis and computer programming. The probability that a given event may occur is calculated by dividing the number of desired outcomes by the number of possible outcomes in a given population. For example, assume the target individual is a male with a low basal cortisol level (less than 11 nMol/L). The probability that the wearer will be male out of the general U.S. population with a female-to-male ratio of 1.07 is P(male)=48.3%. The probability that the wearer will have low cortisol given that (hypothetically) 1 of 25 individuals in a population typically has a basal cortisol level under 11 nMol/L is P(low cortisol)=4%. The combined probability that two independent events would occur randomly, is calculated by multiplying the probabilities. If two identification metrics taken on the wearer indicate that the wearer is a male with low basal cortisol, the probability that a random member of the population would have both identification metrics is 0.483·0.04=1.9%. Therefore, the identification probability estimate that the wearer is the target individual is 98.0%.

For further refinement of the method, each probability estimate may then be weighted appropriately considering each estimate's reliability within the context of the sweat sensing device's capabilities and operation. For example, an analyte trend reading calculated with a limited number of data points would be weighed less than a similar reading calculated from many data points. Similarly, a BMI measurement by body impedance sensors may suffer inaccuracies due to the number of sensors used, the wearer's level of dehydration, or the time proximity of the measurement to food consumption or strenuous exercise by the wearer. As a component of an identification probability estimate, therefore, a BMI measurement would be weighed less than other more reliable metrics. Weighted aggregation of the separate identification probability estimates, then, is a dynamic process, considering, for example, the hydration level of the wearer, sweat rate at the time of measurement, the functionality of sensors, number of operating sensors, number of readings taken, and other relevant factors.

Several identification metrics are available for use with a sweat sensing device, including metrics derived from sweat analytes, metrics derived from other characteristics of the wearer, and metrics derived from data originating outside the wearer's body, such as device communication characteristics or location.

Perhaps the most reliable of these metrics are ones derived from the sweat sensing device's sweat analyte measurements. Accordingly, the device may be configured to create an analyte data signature based on individual differences in analyte concentrations and ratios that emerge in sweat. This analyte data signature may comprise all or part of the target individual's identification signature. The concentrations of different sweat analytes, whether commonly or rarely found in sweat, or the comparative ratios of such analytes, may be a strong indicator of identity. In the simplest case, a sweat sensing device may detect sweat concentrations or ratios of sex hormones, such as estradiol or testosterone, to determine a wearer's sex. In other embodiments, a wearer's resting concentration of $Na^+$ (common) or chromium (less common); a wearer's ratio of common electrolytes, such as the resting ratio of $K^+$ to $Na'$; or a wearer's trend profile of $K^+$ to $Na^+$ when stress sweating or when sweating due to physical exertion, may prove to be effective identifiers of the individual. In other embodiments, apocrine sweat sex-specific pheromones may be used to identify a wearer.

In another embodiment of the invention, the sweat sensing device may be configured to create an analyte signature based on biological oligomers, such as nucleotides, that are excreted in eccrine sweat. DNA fragments, RNA fragments, micro RNA, peptides, and similar oligomers emerge in eccrine sweat, and perform various extracellular signaling functions. In particular, micro RNA appears to play a significant role in exosomic endocrine modulation and mediation of tissue crosstalk, facilitating immune response, among other functions. The concentrations of micro RNA, and/or other biological oligomers in sweat, or the comparative ratios of such oligomers, or the ratios of such oligomers to other analytes, may be a strong indicator of identity.

In an alternative embodiment, a target individual could be administered a tracer compound that can be used to determine if a device wearer is a target individual, for example by incorporating expected tracer-related sweat molecule concentrations into the individual's analyte data profile. After being administered, the tracer molecule or its metabolite(s) are excreted in sweat and detected by the sweat sensing device. The tracer compound may be a substance that is easily detectable in sweat, with known and predictable metabolizing qualities. The tracer compound may be selected with a half-life that is appropriate to the length of time the sweat sensor is to be worn by the user, or the tracer compound may be administered at regular intervals suitable for the duration of sweat sensor use. The sweat sensing device detects the tracer compound in the sweat and compares the detected levels to the expected levels based on the administered dose and/or the half-life. By confirming that the tracer molecule is detected at the expected concentrations in the sweat, the sweat sensing device will be able to calculate a higher identification probability estimate.

Several other techniques that do not rely on sweat analyte data may also prove useful for identifying a user with a sweat sensing device. For example, in another embodiment of the invention, the sweat sensing device may be configured to combine sweat sensing device measurements with data from other wearable sensors currently known in the art, such as an accelerometer, gait analysis sensor, heart rate monitor, sensors measuring electrodermal activity, such as galvanic skin response, pulse oximetry, and others. For example, a sweat sensing device may take analyte measurements of $Na^t$, $Cl^-$ and $K^t$ concentrations as they emerge in a wearer's sweat. The device then uses the trending ratio of $Cl^-$ to $K^t$ and corrects for sweat rate by using the $Na^t$ concentration trend. The device then compares these analyte values to the analyte signature assigned to a target individual. The device determines that the measured values correspond to the analyte signature, giving a (hypothetical) 70% probability that the wearer is the target individual. The device then accounts for measurements from a gait analysis device, which determines that the wearer's gait matches that of the target individual with a (hypothetical) probability of 70%. The sweat sensing device then calculates a weighted average of the two probabilities to calculate a combined probability estimate of 91% that the wearer is the target individual.

In other embodiments, a sweat sensing device may use impedance electrodes to calculate the body mass index (BMI) or body composition of a device wearer. BMI readings vary from individual to individual depending on their sex, age and fitness level, among other factors. In some cases, the composition or thickness of layers of fat under skin could be measured by impedance, since the resistance to electricity varies between adipose, muscular and skeletal tissue. A body composition reading could be used to determine whether a child, a middle-aged adult, or an older adult was likely wearing a device, or if a male or female, or someone who is generally fit, or someone who is overweight is wearing it. A sweat sensing device or other means may be used to develop a BMI signature that comprises all or part of a target individual's identification signature. The individual may also be periodically reassessed to ensure the BMI signature is accurate. A device may then accomplish a BMI measurement on a wearer, and compare the measurement to the BMI signature on file for a target individual to determine the identification probability estimate for the wearer.

Similarly, in other embodiments, the sweat sensing device may be configured to calculate the skin age or skin pigmentation of the individual wearing the device using skin impedance readings. An optical sensor could also be used to detect skin pigmentation, using hardware in some cases similar to that used for pulse oximetry. Skin impedance readings vary predictably according to an individual's age with the amount of scarring of tissue over time, with hydration, with increase in skin roughness, change in the level of function of eccrine sweat glands, or other known factors. Likewise, the ratio of pigment molecules to other molecules contained in the skin varies from individual to individual. As in the case of BMI, a skin type signature may be developed to contribute to a target individual's identification signature.

In another embodiment of the present invention, a sweat response signature may be developed for a target individual based on their typical sweat response to a stimulus. The target individual's sweat response signature would be compared to the sweat response metric generated while the wearer performed a test designed to elicit an electro-physical response, such as a math test or having the wearer count backwards from 100. Sweat response is largely influenced by sweat gland density at the anatomical location of the device's application. In addition, individual sweat rate can change based on the individual's sweat threshold, which may be influenced by physical activity levels or climate. These variations can influence the time it takes to evoke a physiological response to stimulus, as well as the volumetric rate of the response. A target individual may be given multiple tests of this nature to develop a more accurate sweat response signature value, or the individual may be periodically reassessed to update the signature. As with other methods disclosed herein, a target individual's sweat response signature may comprise all or part of the individual's identification signature.

In other embodiments of the present invention, the sweat sensor device may use data originating outside the target individual's body, such as computer network connectivity, or Global Positioning System location data, to create an identification signature. For example, the sweat sensor may be in wireless communication with a reader device, such as a smart phone or other portable electronic device, or a companion transceiver. The reader device is programmed to operate the sweat sensor and to detect the RFID, or other firmware signature of the sweat sensor. The sweat sensor's RFID device or other firmware, is programmed with a unique identification code that indicates the sensor is part of a certain group, or lot, of sensors. The particular lot of sensors may, for example, all serve a particular purpose, or may have been distributed to a specific individual. The sweat sensor, when communicating data to the reader device, would transmit the identification code along with the sensor data. The reader device could then determine if the sweat sensor is part of the correct lot of sensors for the particular individual or application.

Similarly, the sweat sensor may be in wireless communication with a reader device through a wireless protocol such as Bluetooth or other communication strategy. The reader device can determine the signal strength of the sweat sensor, and thereby determine approximate distance from the reader device to the sweat sensor as it is being worn by an individual. The reader device may be associated with an individual or group of individuals. By calculating the approximate distance from the reader device to the target individual, it can be determined if a sweat sensor is being worn in proximity to a device that is associated with a particular individual, thereby increasing the probability that the wearer is the target individual.

In another embodiment, the reader device could determine its approximate location via GPS application, network access location, or other means. When the reader device is in wireless communication with the sweat sensor, it could determine the approximate location of the sweat sensor as an individual is wearing it. By calculating the individual's approximate location, and comparing the calculated location with the target's individual's known approximate location, the sweat sensing device can ensure the device is being worn by the target individual.

In another embodiment of the present invention, a trained professional could apply the sweat sensing device to the target individual and the device would then be activated. If the device were subsequently removed from the target individual, the sweat sensing device could detect the change in impedance indicating device removal.

Figure 5:
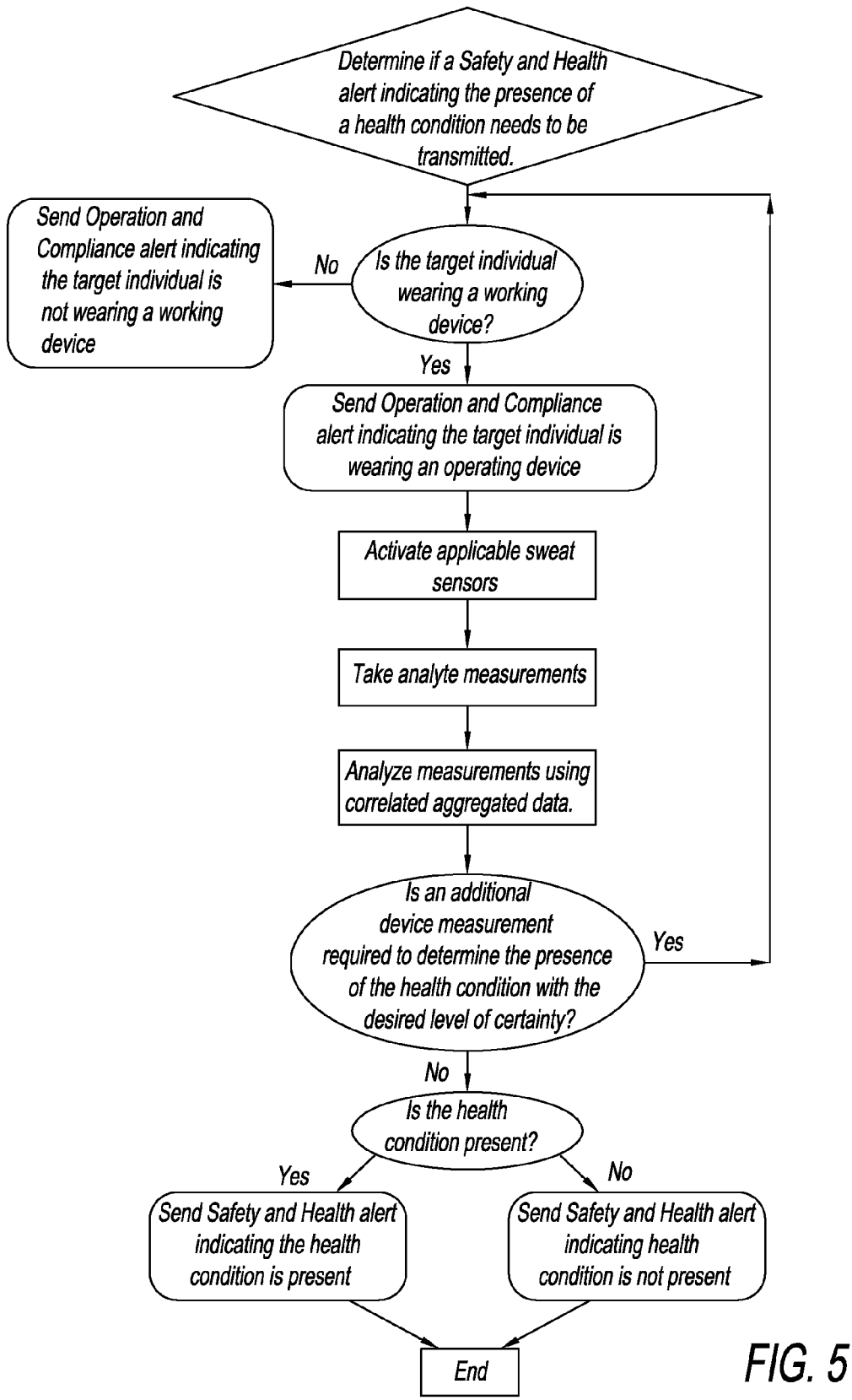
FIG. 5 is an example chart representing a method by which the present invention may determine if the wearer is experiencing a health condition, and issue an appropriate alert.

With reference to FIG. 5, the sweat sensing device could also generate safety and health alerts to warn the device user or the wearer that analyte concentrations, analyte ratios, or trend data for such measurements indicate the need for intervention. As with the operation and compliance alerts, these messages could be communicated in various formats. The device may conduct continuous or periodic safety and health readings to determine if the wearer's detected analytes indicate the need for intervention. Once the device detects a predetermined analyte threshold or trend, the device would generate a safety and health alert, which would be relayed to the device user or to the wearer. Depending on the application, the sweat sensing device user may set threshold or trend criteria for the target individual's hydration level, blood alcohol content, blood sugar levels, level of physiological stress, or other measures within the capability of the sweat sensor device in use. The sweat sensing device could also integrate other aggregated sweat sensor and external data, such as the current weather, the time of day, the individual's previous day exertion level, the number of continuous days the individual was on the job, the individual's historical analyte profiles, and etc., to determine whether to issue a safety and health alert. For example, the sweat sensing device may have access to aggregated data on thousands of individuals of similar age that experienced an analyte profile similar to the wearer under similar environmental conditions. The device could use the aggregated data to predict how long the wearer may have until intervention is required and issue an appropriate alert. The device may also report data to safety, compliance or care managers to identify a wearer that is in need of additional instruction or monitoring as to obtaining optimal physical and mental performance, hydration maintenance, adherence to a drug regimen, or other appropriate applications.

In another embodiment of the present invention, the sweat sensing device could be configured for use in clinical trials to provide improved safety monitoring without the need for blood draws, and to ensure compliance with drug regimens. The devices may be customized for use with a specific drug, or may be for general application to clinical trials.

To monitor safety, the sweat sensor devices may be internally configured to monitor a suite of analytes useful in such trials for safety purposes, such as $Na^+$, $Cl^-$, $K^+$, $Ca^{+2}$, cortisol, glucose, and ammonium, to name a few. Alternatively, the sensor may be configured to monitor specific analytes indicative of side effects identified during earlier clinical studies or animal trials. In addition, the sensor could be configured to monitor the health of specific organs during treatment through sweat detection of metabolic, renal or other similar commonly used blood test panels. The device may also monitor for specific analytes associated with the side-effects or safety implications of a particular drug. For example, drug safety could be monitored by developing an analyte safety profile. The safety profile would consist of analytes that, when analyzed together, indicate with high probability that a test subject needs intervention. A safety profile for a particular drug may be predicted using correlated aggregated sweat sensor data, or it may need to be developed by the device as it is being used during a clinical trial. A safety profile developed for a drug during its clinical trials could then be used to monitor safety post-approval.

To monitor compliance with a drug regimen, the sensor device may be internally configured to detect metabolites or other analytes that are associated with the trial drug, or with a tracer compound having metabolic properties similar to the trial drug. For example, compliance could be monitored by developing a behavioral profile. The behavioral profile would consist of analytes that, when taken together, indicate with high probability that a test subject is, or is not, following a drug regimen. The analytes in the profile may be metabolites of the drug itself, a tracer compound, or they might be other analytes that are indirectly affected by the drug. When a drug is taken, the concentration of various analytes in the bloodstream may change in reaction to the drug. The device could monitor the concentrations of these analytes, the ratio of these analytes to each other, and could develop trend data showing changes in their relative concentrations. The behavioral profile would then be a known set of analyte levels, ratios, or concentration trends that is unique to compliance with a particular drug regimen. A behavioral profile for a particular drug may be predicted using correlated aggregated sweat sensor data, or it may need to be developed by the device as it is being used during a clinical trial. A behavioral profile developed for a drug during its clinical trials could then be used to monitor compliance post-approval.

If the analytes monitored for safety purposes indicated the need for intervention, the device could generate and communicate a safety and health alert. Similarly, if detected analyte readings differed significantly from the drug's behavioral profile, the device would determine that the target individual had not taken a required dose, and could generate and communicate a safety and health alert.

Figure 6:
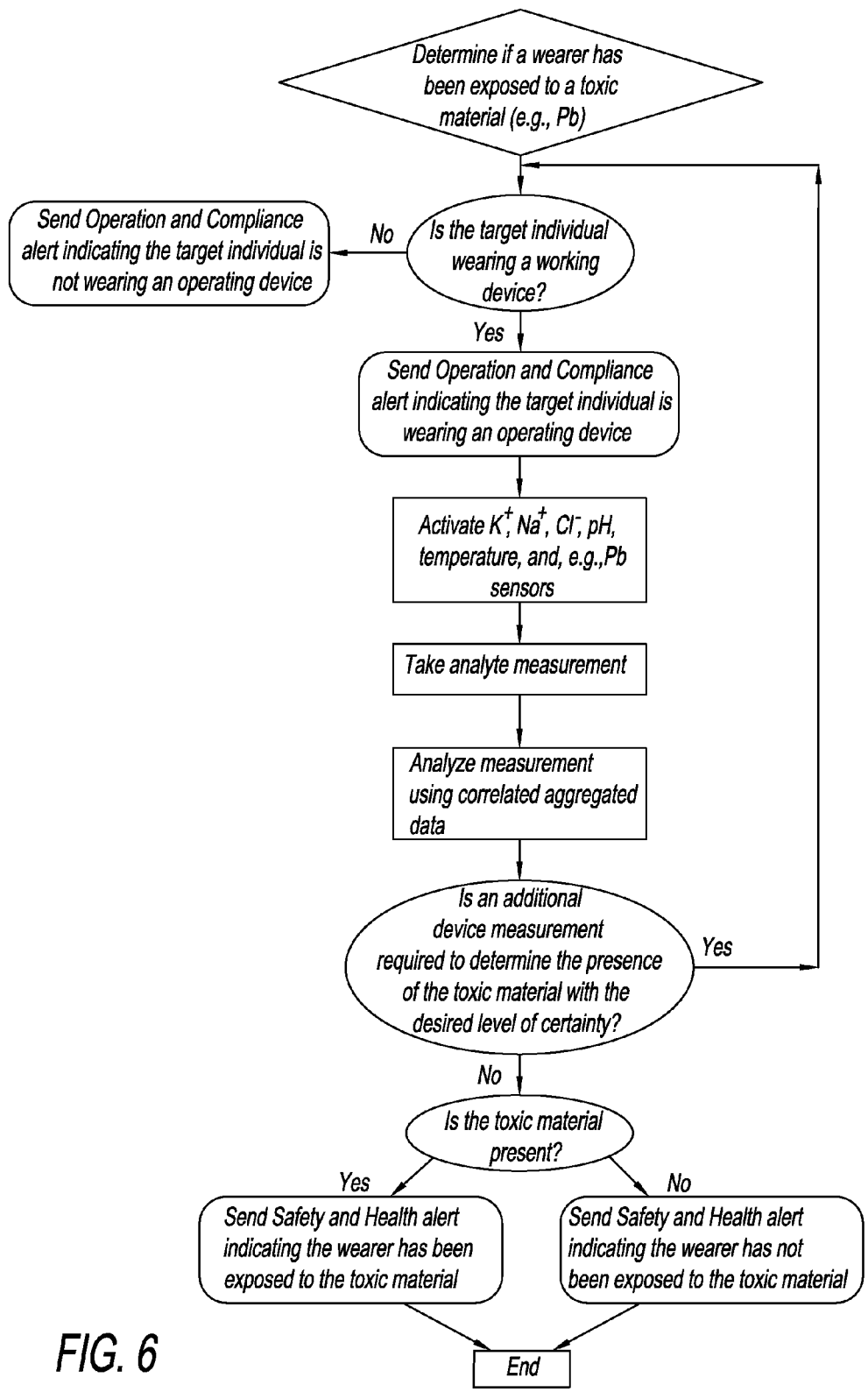
FIG. 6 is an example chart representing a method by which the present invention may determine if a wearer has been exposed to a toxic material.

With reference to FIG. 6, in another embodiment of the present invention, the sweat sensing device could be configured to enhance workplace safety by providing continuous or near-continuous monitoring for the presence of workplace-related toxins in a wearer's bloodstream. Sweat has been identified as a preferential means of monitoring for the presence of toxic metals, metalloids, petrochemicals and other substances, since bioaccumulation levels of such toxins may be underrepresented in blood and urine. The devices may therefore be internally configured to detect toxins that are widely encountered in workplace settings, or may be customized to detect toxins that are unique to a particular workplace. As with safety monitoring in other contexts, for workplace safety a device may be configured to monitor for specific analytes associated with exposure to a particular toxin, or group of toxins. For example, workplace safety could be monitored by developing an analyte safety profile for the workplace. The safety profile would consist of analytes that, when taken together, indicate with high probability that an employee needs intervention from exposure to toxins. A safety profile for a particular workplace may be developed using correlated aggregated sweat sensor data, or it may need to be developed by the device as it is being used. Further, an individual's toxin exposure data may be stored and monitored over time, and factored into future safety and health alerts for that individual.

Wearable digital health devices are dominantly found in rigid form factors such as bracelets and pucks. An adhesive RFID sensor bandage (patch) is reported, which can be made completely intimate with human skin, a distinct advantage for chronological monitoring of biomarkers in sweat. In this demonstration, a commercial RFID chip is adapted with minimum components to allow potentiometric sensing of solutes in sweat, and surface temperature, as read by an Android™ smart-phone app with 96% accuracy at 50 mM Na+(in-vitro tests). All circuitry is solder-reflow integrated on a standard Cu/polyimide flexible-electronic layer including an antenna, but while also allowing electroplating for simple integration of exotic metals for sensing electrodes. Optional paper microfluidics wick sweat from a sweat porous adhesive allowing flow to the sensor, or the sensor can be directly contacted to the skin. The wearability of the patch has been demonstrated for up to 7 days, and includes a protective textile which provides a feel and appearance similar to a standard Band-Aid®. Applications include hydration monitoring, but the basic capability is extendable to other mM ionic solutes in sweat (Cl—, K+, Mg2+, NH4+, Zn2+). The design and fabrication of the patch is provided in full detail, as the basic components could be useful in the design of other wearable sensors.

I. INTRODUCTION

Sweat is one of few examples of non-invasively accessed biofluids, with potential advantages in measurement of inflammatory biomarkers compared to saliva and potentially superior time-resolved (chronological) readings of biomarker concentrations compared to saliva and urine. Sweat access can be locally stimulated using FDA-approved iontophoresis (Wescor Macroduct), and recent tattoo-like sweat-sensing demonstrations further include measurement of lactate, ammonium, and sodium [2-4]. A particularly attractive application could be hydration and heat-stress monitoring through electrolyte balance (e.g., Na+, K+) for athletes, military personnel, first-responders, and others working in extreme-conditions. Electrolyte sensing is of further value, because the high salinity of sweat can confound other biomarker readings, hence electrolyte concentrations need to be base-lined. Realizing such wearable sensors could be achieved several ways, including wearable textiles, tattoos, and form-factors such as those seen commercially in digital bracelet products such as Nike+™ and Fitbit™. However, a complete wireless sensor with wearability comparable to a simple Band-Aid® that is low cost, robust, communicates with smart phones and exhibits a design which automatically lends itself to maximum time-resolved readings of sweat has not yet been demonstrated.

A wearable, medical-grade adhesive RFID enabled sensor patch is reported, which is conformal to the shape of the human body, and therefore minimizes dead volumes of sweat which would otherwise limit chronological measurements. Adaptation of a commercial RFID chip is achieved with minimum components to allow potentiometric sensing of electrolytes in sweat as well as skin surface temperature, and could be of use for hydration and heat-stress monitoring. The patch is battery-free, powered and read wirelessly by an Android smart phone and custom-app. From in-vitro solution to smart-phone readout, a dynamic range of 235 mV to 255 mV is achieved with 20 mM to 70 mM range and 96% accuracy in the detection of Na+ concentration. All circuitry is solder-reflow integrated on a standard Cu/polyimide flexibleelectronic layer including conventional components such as an antenna, but also allowing electroplating for simple integration of exotic metals for ion-selective sensing electrodes. The sensing electrodes can be folded over to be in direct contact with skin, or paper microfluidics can be used to wick sweat from the skin and to the sensors. The wearability of the patch has been shown up to 7 days, and includes a protective textile which provides a feel and appearance similar to a standard Band-Aid or transdermal patch. This work outlines a complete integration of the key materials, electronics, microfluidics, and ergonomics, required for a wearable sweat sensing patch, paving the way for future wearable sweat sensor development and in-vivo testing. Applications include hydration monitoring, but the basic capability is extendable to other mM solutes in sweat (Cl—, K+, Mg2+, NH4+, Zn2+). Full details of the design and fabrication of the patch are reported, as the basic components could be of use to other wearable sensor applications. A preliminary version of this work has been initially accepted as proceedings of IEEE EMBC'14.

II. TOP-LEVEL DESIGN CONSIDERATIONS

A. Patch Size

Two patch sizes were chosen and demonstrated. The smaller size (~25×60 mm) of a typical Band-Aid was used for high user acceptance. A larger 70×40 mm patch was also demonstrated, a size similar to bandage that might be placed over a knee. To allow a maximally thin form factor, potentially longer shelf-life, and low cost, the patch was designed for battery-free RFID (radio-frequency ID, inductively powered) operation. RFID requires ~10-20 loops of a coiled antenna to power the electronics (depending on patch size). The resulting area interior to the coil is more than sufficient for placement of the necessary electronics and the sensor electrodes (as visible in FIG. 7). The larger of the two patch antenna sizes was found to be more resilient to variations in antenna fabrication (antenna resonance), and provides greater reliability in communication. Patches even smaller than those demonstrated here are possible (see online supplemental file on antenna design).

B. Communication

For communication, most modern smartphones have, or will have, the capability to establish wireless connections and transfer data via a near-field communication RFID protocol. The patch is designed to operate on the standard ISO-15693 as a vicinity device. This provides the desired versatility in communication through stand-alone RFID readers as well as customizable applications ('apps') for RFID-enabled Android smartphones. The ubiquity of smartphones provides an easily accessible computing platform with increased memory/storage capabilities, thereby eliminating the need for on-patch data logging and the additional circuitry, cost, size it would require.

C. Flexible & Wearable

Flexibility is of paramount concern in wearable electronics, along with strength and durability. The flexible printed circuit board (PCB) is built from Dupont Pyralux—a combination of flexible, conformal polyimide 812 and a thin copper foil 816. The high heat tolerance of the polyimide allows for electronics to be attached by solder reflow. Furthermore, solder reflow allows surface-mount packaging which eliminates need for throughholes that would result in protrusions that would cause discomfort when the patch is worn. For packaging and skin adhesion, a survey of numerous medical-grade textiles from 3M™ was conducted to determine which materials would provide maximum adhesion to the wearer's skin and high durability to protect the patch itself. Double sided medical adhesive tape was used below the patch, whereas above the patch, a medical textile covering was added to protect the patch and improve visual aesthetics (all shown in FIG. 8).

D. Basic Electronics and Programming Functionality

The system level block diagram illustrates the system level layout of the patch functionality beginning and ending with communication between the reader device and the patch. The reader device initiates the communication and requests identification from the patch. The patch responds by load modulating the inductive coupling between itself and the RFID reader. Custom commands for programming include reading, writing to memory registers, sensor configuration, power management, and other functionalities not required for this present work.

The primary chip in the patch is a small Melexis MLX90129 RFID transponder chip which has both basic sensor and energy harvesting capabilities. The chip functionality is explained in detail here, because its use could be adapted to a large variety of other sensor applications. A significant amount of programming development was required to enable a smart phone to turn the RFID chip into an electrolyte sensor. The sensor protocol manages tasks assigned to the MLX90129's sensor pins such as input connections, voltage output to external sensors, and enabling the internal temperature sensor. Four input pins provide differential measurement of potential from externally connected sensors (e.g. ion selective electrodes in this work). Two internal connections can enable the output of the onboard temperature sensor to be used as input into the multiplexer. Configuration of the multiplexer determines which inputs are passed to the first programmable gain amplifier (PGA). If enabled, the digital to analog converter (DAC) can set the offset used in the optional second PGA. The 12-bit ADC converts the amplified sensor outputs for storage in digital memory until the DAC converts the digital measurements for analog transmission to the reader.

Battery-free operation is achieved by utilizing energy harvesting circuitry of the MLX90129, 724 (FIG. 7) which utilizes the induced current of the incoming electromagnetic waves from the reader to power the entire patch. To facilitate the power demands of the various IC processes, an external capacitor 712 and diode 716 are added for charge storage. The siphoned charge is used to complete low power processes during brief interruptions or absences of induced current from the reader device. Battery independence improves the potential shelf-life of such patches.

III. DETAILED FABRICATION—ELECTRONICS

1) Flexible Circuit Board

Fabrication begins at the flexible electronic circuit board (FIG. 7) with a sheet of Dupont Pyralux AC (18 µm thick Cu foil clad to 12 µm Kapton). A 127×101.6 mm substrate is first cut from the bulk Pyralux roll. As the integrity of the copper surface is imperative, great care must be taken to minimize creases, dimples, and other surface imperfections. Therefore even during substrate cleaning, the substrate is supported by a rigid silicon carrier. The substrate is cleaned of any residual oils, fingerprints or other contaminants by submerging it in a 120° C. alkaline solution of $Na_2CO_3$ (9.2 wt %), 50% NaOH (4.6 wt %), Triton X-100 (surfactant, 0.2 wt %) and reverse osmosis (RO) $H_2O$ (86.0 wt %). The sample is left in the solution for a minimum of 10 min and agitated approximately every 2 to 3 min, and then rinsed thoroughly in RO water. Once rinsed and dried in $N_2$, the substrate is then placed in a bath of reagent grade $H_2SO_4$ (10 wt %) for 5 min to remove the manufacturer's anti-tarnish coating and prepare the sample for lithography. As before, the copper is thoroughly rinsed in RO water and dried in $N_2$.

To pattern the Cu, Shipley S1818 positive tone, liquid photoresist is coated on the copper substrate using traditional spin-coat techniques. For the spin-coat process, the substrate is bonded to 6 inch silicon wafer using a droplet of water, smoothed via a plastic blade for uniform pressure, and held in place by capillary adhesion.

The S1818 resist is spun first at 500 rpm for 30 s and then at 2500 rpm for 60 s to achieve a target thickness between 2 to 2.5 µm (a thicker resist is more durable during the etching process). The substrate and the Si carrier are then "soft" baked in an oven set at 100° C. for 150 s. The carrier and copper substrate are removed from the oven and allowed to cool briefly before masking and 365 nm UV exposure at 150 $mJ/cm^2$ for 25 s. Developing of the resist is accomplished by placing the substrate and carrier for 45 s into an agitated ~21° C. bath of Microposit 351 photoresist developer diluted with RO to a 1:4 (v/v) ratio. This solution is slightly more aggressive than the more common 1:5 ratio, however, the higher concentration developer performs better at removing the exposed photoresist from the non-uniform features of the copper surface and therefore results in a more consistent etch time and cleaner etch results. During development of the photoresist the Si carrier detaches from the substrate so that great care must be taken during rinsing and drying of the substrate after development.

Etching of the exposed copper is accomplished by an air bubble agitated acid bath in which the substrate is secured with PTFE screws to a plastic acrylic carrier and submerged vertically positioned for 30 s. The acid bath is comprised of a diluted reagent HCl solution (30 wt %) and diluted solution of 30% $H_2O_2$ (3 wt %) combined at a ratio of 2:1 by volume. After etching is complete, the substrate and carrier are thoroughly rinsed in a spray of RO water for a minimum of 60 s and dried using compressed $N_2$. The substrate is then carefully removed from the acrylic carrier and placed on the Si wafer for photoresist stripping. The S1818 photoresist is removed by submerging the sample and Si carrier in a bath of full concentration Shipley 351 photoresist developer. The bath is manually agitated once every 30 s for 5 min or until all the photoresist has been removed from the Cu surface. A final rinse and dry step is performed and electrical continuity tests are used to verify the integrity of the antenna coil 704 traces, sensor electrode traces and other critical connections.

2) Plating of Sensor Electrodes

Figure 7:
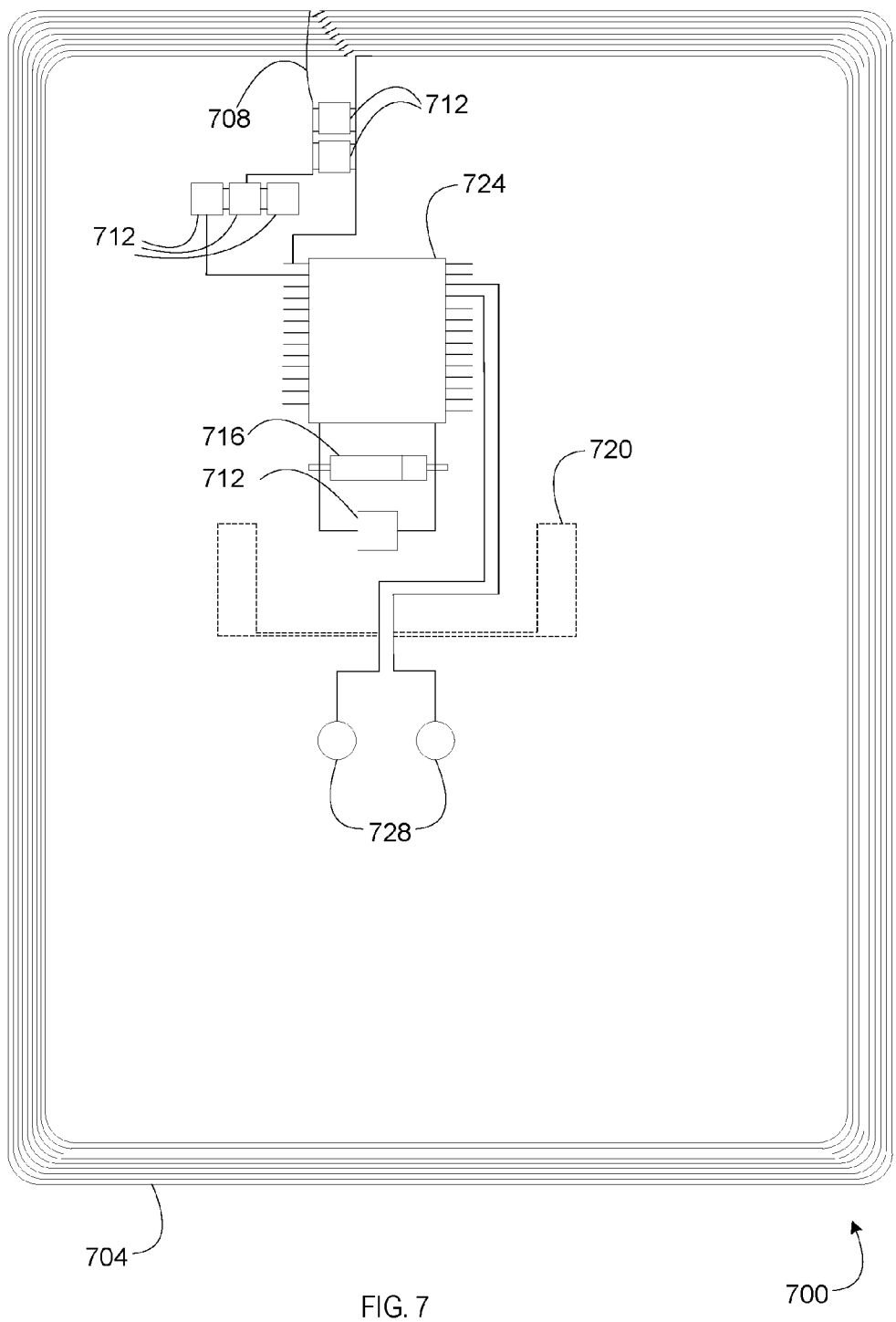

The sensors are fabricated in two steps, one before and one after the electronic chip attachment. In the first step, the working and reference electrodes of the sensor (FIG. 8*a*) are fabricated by electrodeposition of Pd and Ag on the previously-defined bare copper electrodes 728 (FIG. 7). This is accomplished using plating solutions from Technic, Inc. and deposition at ~5 $mA/cm^2$ anodic current for 90 s with a Pt wire auxiliary electrode to sustain the current. The reference electrode fabrication is then completed by chloridization of the Ag layer in 1 M KCl with a 3 mA/cm2 anodic current for 30 s to form the reference.

3) Chip Attachment

Before chip attachment, the inductance of the antenna coil is measured to determine the needed values of the tuning capacitors 712 shown in FIG. 7. An alloy of Sn/Ag (96.5/3.5%) noclean solder paste (Superior Flux & Mfg. Co. P/N: 3033-85) is applied to each pad using an air-metered syringe dispenser, or higher volume fabrication by stencil printing. The chips are then placed, and also an insulated jumper wire 708 (FIG. 7) is placed to connect to the outer loop of the coil 704. The flex circuit board is then placed in a programmable, convection reflow oven that applies a heating profile according to the solder supplier specification. The reflow oven is connected to a pressurized N2 gas supply, which is used to purge the sample chamber and prevent oxidation of the Cu surfaces.

4) Hermetic Sealing of Electronics

In applications where fluid contact could occur, such as sweat sensing, the electronics must be hermetically sealed. This is easily achieved by masking the sensor electrodes with Kapton Tape (silicone adhesive), and conformally coating the flexible circuit and electronics with 10 s of μm of Parylene C polymer dielectric using a Specialty Coating Systems 2010 Lab Coater. Ideally this is performed before sensor functionalization, to ensure the Kapton masking tape does not damage or contaminate the final sensor surfaces.

5) Sensor Functionalization

Onto the plated sensor electrodes, the polymer ionophore (ion-selective) membrane is cast. This is performed after chip attachment because the high temperature required for chip solder reflow would damage the polymer membranes. The membrane solution was cast carefully over the working electrode using a modified screen printing process. The membrane was made from a cocktail of sodium ionophore X, bis(2-ethylhexyl) sebacate (DOS), potassium tetrakis (pchlorophenyl) borate (KTpClPB), PVC, and cyclohexanone, then manually mixed together until the PVC was fully dissolved. The cast membranes were left to air dry for 8 hours, then coated 2 more times to ensure adequate coverage of the electrodes and to passivate any pores in the membrane that could cause shorting to the electrodes.

The Na+ sensor is based on a traditional ion selective electrode (ISE), but which has been miniaturized in this work. The Na+ selective ionophore membrane establishes a difference in potential across the electrode-ionophore barrier corresponding to the Na+ concentration, enabling a simple potentiometric measurement. The level of Na+ in the solution is given by the Nernst equation: $E=E_0+S\log(X)$, where E is the measured electrode potential, $E_0$ is the reference electrode potential, S is the sensitivity, and X is the concentration of Na+ ions in solution. Although in this work only sensing of Na+ is demonstrated, sensing of other ions in sweat (Cl—, K+, Mg2+, NH4+, Zn2+) could be demonstrated using appropriate commercially available ionophores from Sigma Aldrich.

6) Substrate Cutting

The patch is a wearable sensor, and therefore all unused portions of gas/liquid impermeable polyimide substrate film should be removed to provide skin access, and to improve breathability of the final patch. Cutting is performed using a Universal Laser Systems VLS3.50 CO2 laser cutter. The areas that are trimmed include area outside the antenna coil, and the unused interior portion, including the electroplating leads 720 (FIG. 7).

IV. INTEGRATION—ELECTRONICS, TEXTILES, SKIN ADHESIVES, AND MICROFLUIDICS

As shown in FIG. 8, the final device (800) integration involves from the bottom up: skin adhesives 808, electronics 812, 816, and 820, paper microfluidics 832, and a vapor porous top adhesive textile 824. All of these layers are laser cut. The bottom, double-sided adhesive layer is 3M™ Double Coated Polyester Tape (P/N: 1567) and cut to a 1 mm offset larger than the trimmed flex circuit layer. An array of circular pores is also laser cut in the bottom adhesive layer to facilitate sweat 828 transmission to the sensor. The microfluidic paper layer is interior to the coil and surrounds the sensor electrodes and electronics. If the sensors are placed face-up (away from skin 804) then they are covered by the paper layer to bring sweat to the sensors. Extensive wearability studies have not been performed with the patch in this initial demonstration, and in the event that further breathability is needed by skin areas covered by flexible circuit substrate, then the paper-microfluidics layer can simply be integrated beneath the electronics layer to provide horizontal transport of vapor or fluid. The top protective layer is cut from 3M™ Tan Polyurethane Tape (P/N: 9834T) with single-sided adhesive. This layer is cut to the same outer dimensions as the bottom adhesive layer to provide an edge sealed seam for the completed patch.

Multi-layer integration is assisted by a custom alignment jig and vacuum forming/bonding table (1 atm. pressure). The bottom layer is affixed to a waxed paper carrier. The flex circuit's sensor electrodes are then folded back and underneath its traces so that the active area of the sensor will be facing the skin. The flex circuit is placed on top of the bottom adhesive layer using the vacuum placement tool. Next, the microfluidic paper layer is placed between the coil and the rest of the circuitry. Finally, the top protective layer is aligned and placed by vacuuming; sealing the circuit and sensor within. A final communication test with the RFID reader is performed to verify operation, and the sweat sensor is ready for programming and use.

V. EXPERIMENTAL TESTING AND RESULTS

A. Wearable Antenna Performance

The assembled RFID circuit was tested to ensure that the resonate frequency was near enough to the target frequency of 13.56 MHz that the device would communicate with the reader. A supplemental information document is provided with the online materials for this paper, detailing the finer details of the antenna design and tuning. To confirm antenna tuning, a vector network analyzer (VNA) was connected to an ISO standard calibration loop-probe, per ISO10373-7, to enable contactless measurement of the patch's frequency response. The VNA displays the loop-probe's reflection coefficient by measuring the S-parameter S11 as a function of frequency. A reduction in the reflection measured by the VNA correlates to an increase in transmission of the electromagnetic waves at a specific frequency, via absorption of the radiated energy by a tuned and coupled device. Successful tuning of the flexible RFID circuit was confirmed by a reduction of S11 by −2.9 dB at 13.56 MHz. With a reader RF power of ~0.5 W this tuning was also shown to be adequate to inductively power the electronics and enable RF communication. Patch communication was shown in wearable format, including arm placement which induces curvature on the entire patch.

B. Sensor and Electronics Performance

Figure 8A:
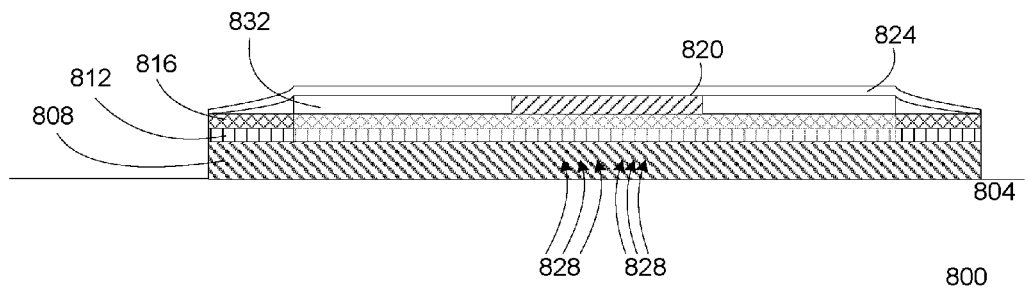
Figure 8A:
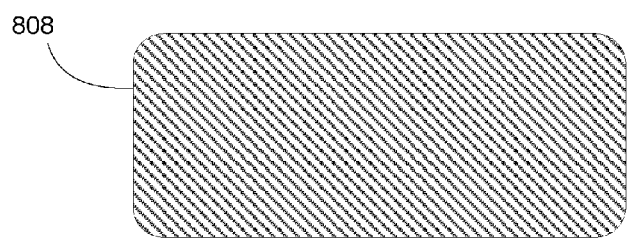
Figure 8A:
Figure 8B:
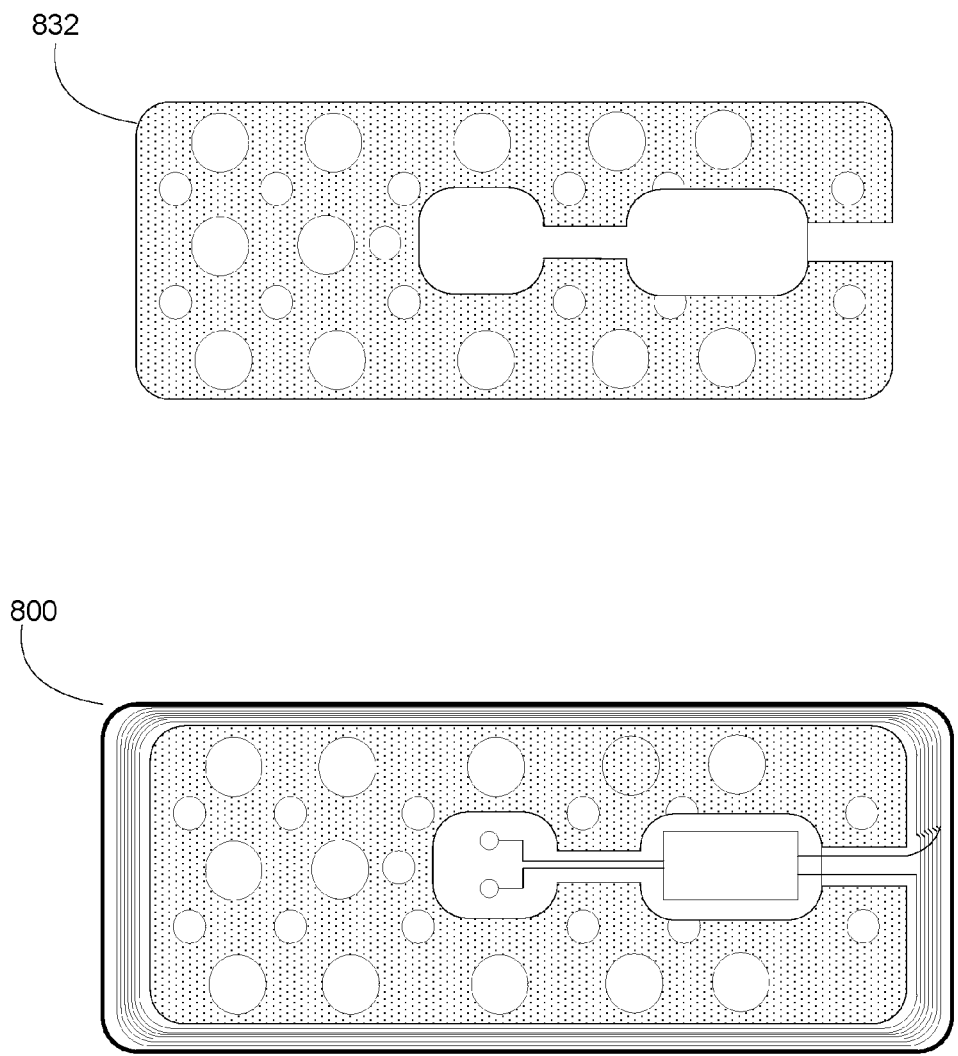

The patch and sensors were characterized in-vitro by pipetting of various NaCl concentration solutions onto the patch sensor. FIG. 8a-8b illustrates sensor response as Na+ concentration increased from 20 mM to 70 mM. As expected, the sensor output increased with analyte concentration, exhibiting stable response at each concentration. At each concentration change, the sensor responded rapidly, with approx. 30 s response time. The standard curve, developed by measuring response of a stand-alone sensor in the 20-70 mM Na+ range against the commercial ISE from Denver Instruments (300741.1) exhibited a correlation coefficient of 0.99 (data not shown). These results clearly suggest that our sensor exhibits acceptable and predictable behavior for measurement of Na+. As expected, the patch-integrated sensors exhibited a predictable linear response, with the correlation coefficient of 0.92. The range of 10 mM to 90 mM was chosen to ensure the detection range would be +/−10 mM beyond physiologically relevant ranges for hydration monitoring.

Sensitivity of the sensor in the integrated patch was 0.3 mV/mM, which was slightly lower than that the commercial sensor sensitivity of 0.5 mV/mM or approx. 25 mV/decade of Na+ concentration. While at first glance this suggests a sub-Nernstian behavior, we tested the stand-alone sensors, and obtained sensitivity of approximately 57 mV/decade of Na+ in the 10-90 mM concentration range, indicating that the sensor exhibits Nernstian behavior. Similar results have been reported for Na+ ISEs by others. Thus, the apparent lower sensitivity of the patch-integrated sensors appears to be due to the limitations of the ADC on the RFID patch. The ADC reference voltage is set by the MLX90129's internal regulator, from which two values may be selected—normal reference of 3.1 V, or low-volt reference of 2.1 V. The minimum voltage of the chip's coil input is such that provided the chip powers on, the internal regulator will supply a stable reference to the ADC. However, since the sampling rate for the converter is slow (<3 Hz) for the desired accuracy the stabilization of the reference electrode on a specific voltage is impaired. The sampling rate used in FIG. 7 is approximately 3 Hz to achieve maximum resolution, while the maximum sampling rate of the device is approx. 435 Hz at the lowest conversion resolution.

Accuracy is an important characteristic for a sensor and measures how close the sensor is able to determine the true value of a given concentration. To measure accuracy of our RFID Na+ sensor, we repeatedly measured 50 mM of NaCl (n=7), which was expected to yield 185 mV based on the calibration curve. Response of our patch was measured to be 177+/−5 mV. These results show that at 50 mM NaCl, our patch sensor exhibits 96% accuracy. Precision is another important characteristic for a sensor and in essence it illustrates sensor variability. From the experimental data, the patch sensor exhibited 28% precision. However, precision is not provided for commercial ISEs, and the needed values will depend on application. Even simple measurement of trending (increase or decrease) of Na+ itself is valuable, as Na+ concentration predicts sweat rate as it increases by 10's of mM in concentration with increasing sweat rate. This patch therefore can be utilized even in its current form as an athletic exertion sensor, for example.

To further explore the potential for continuous monitoring in sweat, concentration of NaCl was varied repeatedly every 4 min from 20 mM to 70 mM over a period of 45 min. Na+ concentration in sweat can vary from 20 mM to 70 mM depending on body hydration status. As shown in FIG. 7, the sensor exhibited good repeatability and stability during this measurement. The average high measurement was 255 mV, which corresponds to 70 mM based on the calibration curve. The coefficient of variation across the 6 high concentration measurements was CV=0.1%, indicating excellent repeatability. Similarly, the 5 low concentration measurements yielded approximately 237 mV, with CV=0.8%. The response time at low concentration was slower, and is a function of the mass transport across the sensor ionselective membrane. As with most electro-chemical sensors, stability of the reference electrode can be an issue and can lead to the inability to collect stable data. Our sensor exhibited only a slight drift (+/−3 mV/5 mM), however by increasing sampling frequency and averaging the values we were able to compensate for this difference. Future work will involve further stabilizing of the Ag/AgCl reference electrode to increase stability of the measured values. Collectively, these results suggest that the developed sensor is suitable for sweat electrolyte monitoring.

VI. DISCUSSION AND CONCLUSIONS

The primary objective of this work was to demonstrate the complete integration of the components and functionality needed for a low-cost and highly self-contained sweat sensor. A collection of key performance data and cost-estimates is provided in Table 1. The most expensive single component, is the Melexis RFID chip, at <$2 in volume purchasing right now. The remainder of the components and fabrication procedures for the patch are rather simple and implementable on most flexible and printed electronics manufacturing lines. Therefore the basic patch presented here could be speculated at this time to meet the economic considerations of a disposable commercial product.

The key question in the applied value for this work is in terms of performance. The performance for the existing patch is shown to be adequate and accurate for basic sensing at physiological relevant levels in sweat, and would increase in performance with higher sampling frequency, improved power management, sensor signal conditioning and conversion efficiency of the analog sensor inputs. Establishing the basic functionality shown in this paper is important, because numerous other ionophores and ion selective electrodes, or measurements, could be integrated with the patch, allowing a broader range of applications for the sensor. The current sensor measures Na+, and using the second sensor port to measure K+ would be intended to explore ratios of electrolytes in relation to hydration (hence the term, 'electrolyte balance'). Other ions of interest include Cl—, Mg2+, NH4+, which expand the physiological readings that could be made from human sweat. Devices such as this, and others, could mark the beginning of an entirely new way of monitoring human physiology and performance. Wearable and wireless devices that are unobtrusive to the user fill a critical gap in the technology needed to collect real time data on the health status of our most precious assets—people.

The following examples are provided to help illustrate the present invention, and are not comprehensive or limiting in any manner These examples serve to illustrate that although the specification herein does not list all possible device features or arrangements or methods for all possible applications, the invention is broad and may incorporate other useful methods or aspects of materials, devices, or other embodiments that are readily understood and obvious for the broad applications of the present invention.

Example 1

A sweat sensor device is used by an employee in a mining operation. When the employee arrives at work for his shift, he applies a sweat sensor device that is coded with a unique identifier assigned to him. After the employee clocks in, the employer's on-shift system determines that he is on the job and the device takes an operation and compliance reading. The device communicates to the device user that the employee's device is in good skin contact. Then the device initiates sweat measurements, and determines that the device is operating on the employee's skin because $Na^+$ and $Cl^-$ concentration trends are as expected for the measured sweat rate. The device also calculates an identification probability estimate by comparing the identification metrics to an identification signature on file for the employee, and determines that the correct person is wearing the device. Four hours into the employee's shift, the device generates a safety and health alert based on the employee's hydration level and trend data. The employee receives the alert via companion transceiver located in his work area, and the supervisor receives an email at his workstation. The employee stops work to rehydrate, and the supervisor schedules the employee for safety training because this was the third instance of serious dehydration the employee experienced in the past month.

Example 2

A professional cyclist is participating in a multi-stage race, and is wearing a sweat sensor device during a 100 mile climbing stage. The device communicates via Bluetooth to a companion transceiver, which in turn communicates via cellular network with the team chase car. During the latter portion of the stage, the sweat sensing device initiates an operation and compliance reading, and determines the device is in good contact with the cyclist's skin. Then the device takes a reading on a group of selected analytes to measure fatigue, hydration level, and inflammation. The device compares the readings to predetermined thresholds representing optimal performance, then creates trend data by comparing the readings to the cyclist's prior readings during that stage. The device then compares the cyclist's current analyte profile and trend data with the cyclist's historical analyte profiles and trend data for similar stages of past races. The sweat device data is then used to generate a safety and health alert to the chase car. The cyclist's chase team then recommends an optimal pace, water and nutrient intake to the cyclist to optimize performance.

Example 3

A group of soldiers in a hot climate is attempting to secure a dangerous area in order to protect a group of civilians, and they are using sweat monitoring devices to measure their physical and mental stresses through sweat electrolytes, cortisol and cytokine biomarker measurements. Each soldier carries a companion transceiver integrated into their equipment. The companion transceiver communicates with the device, and communicates via secure datalink to the patrol leader and the unit commander. The soldiers have been on patrol for several hours, and sweat readings for two of the soldiers are trending toward dehydration and high stress. The device issues a safety and health alert for dehydration and high stress levels for the two affected soldiers and communicates the alert to the unit commander, the patrol leader and the two soldiers. The commander instructs the sweat devices to increase the sampling rate for the two distressed soldiers. The soldiers increase their water consumption. The patrol leader factors the condition of the two soldiers into her decision about whether extend the mission duration.

Example 4

A transplant patient is taking an antirejection medication (immunosuppressant) and his attending physician is utilizing the sweat sensing device to monitor the drug levels in the patient's body through the drug metabolites excreted in sweat. The patient is to wear the device 24 hours a day, replacing it only as needed. The sweat sensing device takes periodic readings of the drug metabolites and other relevant analytes in the patient's sweat. The sweat device compares the patient's analyte readings to a standard analyte profile based on aggregated data collected on other individuals who have taken the drug. The device also constructs a profile of the analyte levels of other individuals that share relevant characteristics with the patient and develops a more customized behavioral signature for the patient. The device also builds an individual behavioral signature for the patient over several days of collecting sweat sensor data. The device then compares the detected analyte levels and ratios to one or more of the behavioral signatures developed for the patient. Several days into the treatment regimen, the sweat sensor performs a reading that detects analyte ratios and trend data that significantly differ from the patient's behavioral signature. The device generates a safety and health alert that the patient has missed a dose of medication and communicates the alert to the patient and the patient's attending physician.

Example 5

A cruise ship captain is about to embark with his ship carrying 900 passengers. According to company protocol, captains are required to wear a sweat sensor device while on duty to monitor performance Unfortunately, the captain spent the previous evening at a bar, and consumed too much alcohol to legally operate the ship. Instead of wearing his device, he instructs his first officer to wear one of his assigned devices and he retires to quarters. The device communicates via Bluetooth with various companion transceivers located throughout the ship, and the transceivers in turn communicate with the cruise ship dispatch center. Upon application by the first officer, the device initiates an operation and compliance reading and then compares the reading with the identification signature on file for the captain. While the device ID is positively associated with the captain, several other identification metrics analyzed by the device diverge from the captain's identification signature, and the identification probability estimate is below the acceptable threshold. The device issues an operation and compliance alert that the wearer is not the captain and communicates it to the cruise ship dispatch center.

Example 6

To determine if a sweat sensing device wearer is a target cancer patient, the device measures the wearer's sweat testosterone concentration, which is an identification metric for sex. The device detects testosterone concentrations that correlate with the wearer being male. In this context, male and female individuals are evenly distributed, so the corresponding identification probability estimate is 50%. The sweat sensing device then measures a second identification metric, which is resting sweat concentration of $Na^-$. The measured $Na^+$ concentration corresponds to the target patient's resting rate with a 75% probability. The device then weighs the two measurements, taking into account the testosterone sensor's inherent accuracy of +1-5% of actual sweat concentration, and the daily variability of testosterone for the target individual's age, as well as the Na$^r$ measurement's stronger accuracy rating derived from the Na$^r$ sensor's inherent accuracy of +/−2% of actual sweat concentration, its stability over time, and the consistency of the concentration value over 10 different samples at comparable sweat rates. The device then combines the two probability estimates to calculate a combined identification probability estimate of 85% that the wearer is the target patient, which is above the desired probability threshold. The device then sends an operation and compliance message indicating that the wearer is the target patient.

This has been a description of the present invention along with a preferred method of practicing the present invention, however the invention itself should only be defined by the appended claims.

What is claimed is:

1. A system comprising:
   a first device;
   a second device; and
   an apparatus for sensing and analyzing at least one fluid, wherein the apparatus includes an electronic layer comprising at least one sensor
   wherein the apparatus analyzes at least one biomarker of the fluid, calculates at least one output of the at least one fluid biomarker using at least one algorithm, and transmits the at least one output to the first device;
   wherein the first device transmits the at least one output to the second device; and
   wherein the apparatus further includes:
      a double-sided adhesive layer;
      a microfluidic layer; and
      a vapor porous, top layer;
   wherein the electronic layer is adhered to the double-sided adhesive layer;
   wherein the microfluidic layer is positioned on the same side of double-sided adhesive layer as the electronic layer;
   wherein the microfluidic layer and the electronic layer are substantially equidistant from the double-sided adhesive layer;
   wherein the vapor porous, top layer is placed on and completely covers the microfluidic layer and the electronic layer; and
   wherein the vapor porous, top layer is adhered to the double-sided adhesive layer.

2. The system of claim 1, wherein the apparatus and the first device have real-time or near-real-time two-way communication.

3. The system of claim 1, wherein the second device comprises:
   a computer server, a computing device, a database, or a combination thereof.

4. The system of claim 1, wherein the apparatus is flexible.

5. The system of claim 1, wherein the apparatus is configured to be adhered to mammalian skin.

6. The system of claim 1, wherein the fluid is sweat.

7. The system of claim 1, wherein the at least one biomarker of the fluid includes small molecules, metabolites, and/or electrolytes.

8. The system of claim 1, wherein the apparatus further includes a microcontroller and a transceiver antenna coil; and
   wherein the at least one sensor is an electrochemical sensor.

9. The system of claim 8, wherein the at least one sensor houses electrodes; and
   wherein electrodes comprise silver, copper, platinum, or a combination thereof.

10. The system of claim 1, wherein the apparatus wirelessly transmits the at least one output to the first device.

11. The system of claim 1, wherein the apparatus continuously monitors the at least one biomarker of the fluid.

12. A system comprising:
    an apparatus for sensing and analyzing sweat, wherein the apparatus includes an electronic layer comprising at least one sensor;
    a first device; and
    a second device;
    wherein the apparatus continuously analyzes at least one sweat biomarker in real-time, calculates at least one output of the at least one sweat biomarker using at least one algorithm, and transmits the at least one output to the first device;
    wherein the first device transmits the at least one output to the second device; and
    wherein the at least one sensor has at least one reference electrode and at least one active electrode;
    wherein the at least one active electrode has an ionophore polymer coating;
    wherein the apparatus further includes:
       a double-sided adhesive layer;
       microfluidic layer; and
       a vapor porous, top layer;
    wherein the electronic layer is adhered to the double-sided adhesive layer;
    wherein the microfluidic layer is positioned on the same side of double-sided adhesive layer as the electronic layer;
    wherein the microfluidic layer and the electronic layer are substantially equidistant from the double-sided adhesive layer;
    wherein the vapor porous, top layer is placed on and completely covers the microfluidic layer and the electronic layer; and
    wherein the vapor porous, top layer is adhered to the double-sided adhesive layer.

13. The system of claim 12, wherein the second device comprises:
    a computer server, a computing device, a database, or a combination thereof;
    wherein the apparatus further comprises a microcontroller and a transceiver antenna coil; and
    wherein the at least one sensor is an electrochemical sensor.

14. A method comprising:
    providing an apparatus for sensing and analyzing at least one fluid, wherein the apparatus includes an electronic layer comprising at least one sensor;
    sensing, by the at least one sensor, at least one biomarker of the fluid;
    converting, by the apparatus, the at least one biomarker of the fluid into at least one output;
    transmitting, by the apparatus, the at least one output to a first device; and
    transmitting, by the first device, the at least one output to a second device; and
    wherein the apparatus further includes:
       a double-sided adhesive layer;
       microfluidic layer; and
       a vapor porous, top layer;
    wherein the electronic layer is adhered to the double-sided adhesive layer;

wherein the microfluidic layer is positioned on the same side of double-sided adhesive layer as the electronic layer;

wherein the microfluidic layer and the electronic layer are substantially equidistant from the double-sided adhesive layer;

wherein the vapor porous, top layer is placed on and completely covers the microfluidic layer and the electronic layer; and wherein the vapor porous, top layer is adhered to the double-sided adhesive layer.

15. The method of claim 14, wherein the apparatus is flexible.

16. The method of claim 14, wherein the double-sided adhesive layer is configured to be adhered to mammalian skin.

17. The method of claim 14, wherein the electronic layer further comprises a microcontroller and a transceiver; and wherein the at least one sensor is an electrochemical sensor.

18. The method of claim 17, wherein the apparatus generates a voltage in response to sensing the at least one biomarker; and wherein the microcontroller generates the at least one output by passing the generated voltage as input to an algorithm.

19. The method of claim 17, wherein the at least one output is transmitted from the apparatus to the first device through wireless network communication by the transceiver of the apparatus; and wherein the wireless network communication is via Bluetooth, radiofrequency, or near field communication.

20. The method of claim 14, wherein the at least one output includes concentrations and descriptive statistics; and wherein descriptive statistics includes ratios and/or trends.

* * * * *

UNITED STATES PATENT AND TRADEMARK OFFICE
CERTIFICATE OF CORRECTION

PATENT NO. : 9,867,539 B2  
APPLICATION NO. : 15/362229  
DATED : January 16, 2018  
INVENTOR(S) : Jason Heikenfeld et al.

Page 1 of 1

It is certified that error appears in the above-identified patent and that said Letters Patent is hereby corrected as shown below:

On the Title Page

Column 1, (73) Assignee:, replace "Eccrine Systems, Inc., Cincinnati, OH (US)" with --University of Cincinnati, A University of the State of Ohio, Cincinnati, OH (US)--

Signed and Sealed this  
Sixteenth Day of April, 2019

Andrei Iancu  
*Director of the United States Patent and Trademark Office*